US008707798B2

(12) United States Patent  
Gregg et al.

(10) Patent No.: US 8,707,798 B2  
(45) Date of Patent: Apr. 29, 2014

(54) SYSTEM AND METHOD FOR TESTING A FILLET BOND

(75) Inventors: Paul S. Gregg, Seattle, WA (US); Brian S. Kasperson, Seattle, WA (US); Jack J. Esposito, Auburn, WA (US)

(73) Assignee: The Boeing Company, Chicago, IL (US)

( * ) Notice: Subject to any disclaimer, the term of this patent is extended or adjusted under 35 U.S.C. 154(b) by 47 days.

(21) Appl. No.: 13/531,968

(22) Filed: Jun. 25, 2012

(65) Prior Publication Data

US 2013/0340534 A1    Dec. 26, 2013

(51) Int. Cl.
*G01N 3/08* (2006.01)
*G01N 19/04* (2006.01)

(52) U.S. Cl.
USPC ............................................ 73/826; 73/150 A

(58) Field of Classification Search
USPC ....................... 73/150 A, 828, 826
See application file for complete search history.

(56) References Cited

U.S. PATENT DOCUMENTS

| | | | |
|---|---|---|---|
| 2011/0214497 A1* | 9/2011 | Sellars et al. | 73/150 A |
| 2011/0252742 A1* | 10/2011 | Hand et al. | 52/783.1 |
| 2012/0192638 A1* | 8/2012 | Zelinsky | 73/150 A |

OTHER PUBLICATIONS

Turunen, "Pull-off test in the assessment of adhesion at printed wiring board metallisation/epoxy interface", Microelectronics Reliability, vol. 44, pp. 993-1007. Sep. 5, 2003.

* cited by examiner

*Primary Examiner* — Lisa Caputo
*Assistant Examiner* — Brandi N Hopkins

(57) ABSTRACT

A testing apparatus for characterizing a tension strength of a fillet bond of a test specimen may include a lower fixture and an upper fixture. The test specimen may include a skin component bonded to a stiffener component. The lower fixture may maintain the stiffener component in a fixed position. The upper fixture may engage the skin component at a pair of discrete engagement locations on opposite sides of the fillet bond. The upper fixture may be mechanically coupled to a gimbal joint and may substantially isolate the filet bond from asymmetric bending during application of a tension test load to the fillet bond.

20 Claims, 15 Drawing Sheets

SYSTEM AND METHOD FOR TESTING A FILLET BOND

FIELD

The present disclosure relates generally to structural testing and, more particularly, to testing systems for characterizing the tension test load-carrying capability of fillet bonds between two structural components.

BACKGROUND

Adhesive bonding of structural components provides several advantages over mechanical fastening. For example, adhesive bonding results in a more uniform stress distribution across a bonded joint relative to the stress distribution across a mechanically-fastened joint. In addition, adhesive forms a barrier between structural components which may avoid undesirable effects that may be associated with mechanical joints wherein dissimilar materials are in direct con tact with one another. Adhesive bonding of structural components may also reduce assembly costs and provide increased fatigue life relative to the assembly costs and fatigue life associated with mechanically-fastened joints.

A fillet bond is a type of adhesive bond between a curved surface of one component and a generally flat surface of another component. In a fillet bond, adhesive material forms fillets between the joined components. The thickness of a fillet bond may vary across a bondline between the two components. Advantageously, fillet bonds may provide improved stress distribution in a joint by spreading load in the joint over a relatively large surface area.

For certain assemblies having bonded joints, it may be necessary to qualify the strength- carrying capability of the bonded joints prior to placing the assembly into service. For example, prior to certifying an aircraft, it may be necessary to qualify bonded joints in primary load-carrying structure of the aircraft. Qualifying the bonded joints may include verifying that the margins of safety of the bonded joints are within design limits. The margins of safety may be determined by applying loads to test specimens of the bonded joint wherein the loads simulate actual loads to which the bonded joint may be subjected during the service life of the joint.

Certain structures may be subjected to in-service loads that place a fillet bond in tension pulloff (e.g., out-of-plane) loads. One such structure that may be subjected to tension pulloff loads is a skin panel having a plurality of stiffeners positioned in spaced relation to one another on one side of the skin panel. Each one of the stiffeners may be bonded to the skin panel with a fillet bond extending along a length of the stiffener. During service, the tension pulloff load may be distributed generally uniformly across the skin panel and may cause the fillet bonds to be loaded in tension.

Conventional testing apparatuses for testing the load-carrying capability of bonded joints are generally directed toward flat-bond geometry between two generally planar components. Adhesive material in such flat-bond geometry may have a generally uniform thickness across the bonded joint. Conventional testing apparatuses may include a generally flat backing plate that may be mounted to an outer surface of a test specimen having a flat-bond geometry. The testing apparatus may be mounted within a testing machine. The test specimen may be instrumented with strain gauges so that strain measurements may be recorded during application of a test load. The strain levels may be converted to stress. The test specimen may be tested to failure and the stress levels at failure may be correlated to strength values of the bonded joint.

Unfortunately, conventional testing apparatuses using backing plates may not provide an accurate duplication of the forces induced in a fillet bond. For example, for the above-mentioned structural assembly having stiffeners bonded to a skin panel, tension pulloff loads on the skin panel may induce bending loads in the test specimen at the fillet bonds. Although conventional testing apparatuses may be adequate for applying a tension test load to a fillet bond in a test specimen, the stiffness of the backing plate prevents the generation of bending loads in the test specimen.

A further drawback associated with conventional testing apparatuses is that eccentric or asymmetric loading may be produced in a test specimen. Such asymmetric loading may be caused by manufacturing tolerances of the test specimen, by misalignment of the test specimen with the testing machine, or due to other factors. The occurrence of asymmetric loading may minimize the repeatability of testing conditions across a plurality of test specimens and may compromise the accuracy of test results.

As can be seen, there exists a need in the art for a testing apparatus and method that may substantially duplicate the loading conditions in a fillet bond during application of a tension to the fillet bond. In this regard, there exists a need in the art for a testing apparatus and method capable of accurately inducing symmetric bending in a fillet bond during application of a tension test load. Ideally, the testing apparatus may avoid the need for measuring strain in a test specimen and then correlating the strain to stress for determining the strength capability of the fillet bond.

SUMMARY

The above-noted needs associated with structural testing of fillet bonds are specifically addressed and alleviated by the present disclosure which provides a testing apparatus for characterizing a tension strength of a fillet bond joining a stiffener component to a skin component of a test specimen. The testing apparatus may include a lower fixture configured to maintain the stiffener component in a fixed position, and an upper fixture configured to engage the skin component at a pair of engagement locations on opposite sides of the fillet bond. The testing apparatus may additionally include a gimbal joint mechanically coupled to the upper fixture and configured to substantially isolate the fillet bond from asymmetric bending during application of a tension test load to the fillet bond.

In a further embodiment, disclosed is a testing apparatus for characterizing a tension strength of a fillet bond. The testing apparatus may include a lower fixture and an upper fixture. The lower may maintain the stiffener component in a fixed position. The upper fixture may have a pair of load pins oriented generally parallel to one another and configured to engage an inner surface of the skin component at a pair of discrete engagement locations on opposite sides of the fillet bond. The testing apparatus may include a gimbal joint mechanically coupled to the upper fixture and configured to substantially isolate the fillet bond from asymmetric bending during application of a tension test load to the fillet bond. The engagement locations may be positioned such that fillet edges of the fillet bond are subjected to a moment-shear ratio that is substantially equivalent to the moment-shear ratio at the fillet edges of a structural assembly subjected to a uniformly distributed tension pulloff load Also disclosed is a method of characterizing a tension strength of a fillet bond joining a stiffener component to a skin component of a test specimen. The method may include the steps of placing the test specimen in a testing apparatus, and fixedly positioning a stiffener component of the test specimen. The method may further include engaging the skin component at a pair of engagement locations on opposite sides of the fillet bond, and applying a tension test load to the fillet bond at the engagement locations. The method may additionally include substantially isolating the fillet bond from asymmetric bending when applying the tension test load.

The features, functions and advantages that have been discussed can be achieved independently in various embodiments of the present disclosure or may be combined in yet other embodiments, further details of which can be seen with reference to the following description and drawings below.

BRIEF DESCRIPTION OF THE DRAWINGS

These and other features of the present disclosure will become more apparent upon reference to the drawings wherein like numbers refer to like parts throughout and wherein.

DETAILED DESCRIPTION

Figure 1:
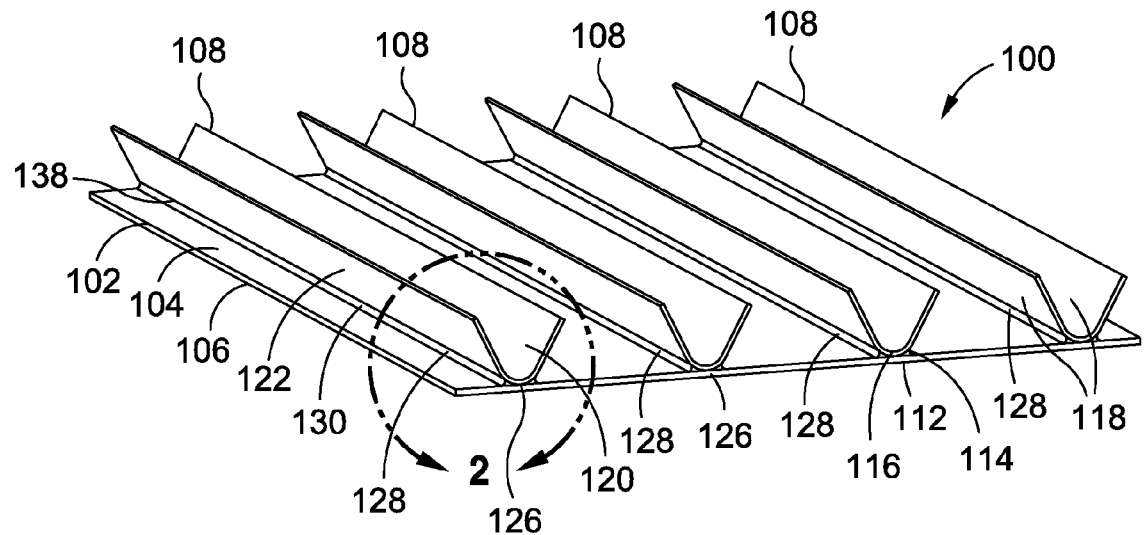
FIG. 1 is a perspective view of a structural assembly having a skin panel in a plurality of stiffeners bonded thereto.

Referring now to the drawings wherein the showings are for purposes of illustrating various embodiments of the present disclosure, shown in FIG. 1 is perspective illustration of a structural assembly 100 having a plurality of panel stiffeners 108 adhesively bonded to a skin panel 102 with fillet bonds 128. In FIG. 1, the skin panel 102 includes an inner surface 104 and an outer surface 106. The panel stiffeners 108 may be bonded to the inner and/or outer surfaces 104, 106 of the skin panel 102. The fillet bonds 128 may extend along a length of the panel stiffeners 108 and may define a skin-stiffener joint 126 for structurally bonding the panel stiffeners 108 to the skin panel 102. Although shown as being generally straight, the panel stiffeners 108 may be curved. The structural assembly 100 may be implemented in any one of a variety of different applications. For example, the structural assembly 100 may be implemented in an aircraft. However, the structural assembly 100 may be implemented in any vehicular or non-vehicular application, without limitation.

The present disclosure provides a testing apparatus 600 (FIG. 11) and a test specimen 300 (FIG. 6) that may advantageously be implemented for characterizing a tension strength of a fillet bond 128 at a skin-stiffener joint 126 of a structural assembly 100. The test specimen 300 may be configured to substantially duplicate the structure and/or geometry of the fillet bond 128 in a structural assembly 100 between a panel stiffener 108 and a skin panel 102. The testing apparatus 600 advantageously provides a means for applying a tension test load 500

(FIG. 13) to a test specimen 300 while isolating a fillet bond 328 (FIG. 6) from asymmetric bending moments 510' (FIG. 25) and/or asymmetric shear forces 512' (FIG. 25) as described in greater detail below. In addition, the testing apparatus 600 also advantageously provides a means for accurately characterizing the tension bond strength of a fillet bond 328 with a high degree of repeatability and with minimal scatter and disparity in test data for a plurality of substantially similar test specimens. The bond strength of the fillet bond 328 may advantageously be characterized in terms of force unit per unit length such as pounds per inch which may facilitate the determination of the margins of safety of fillet bonds 328 for joint qualification and/or aircraft certification.

Figure 2:
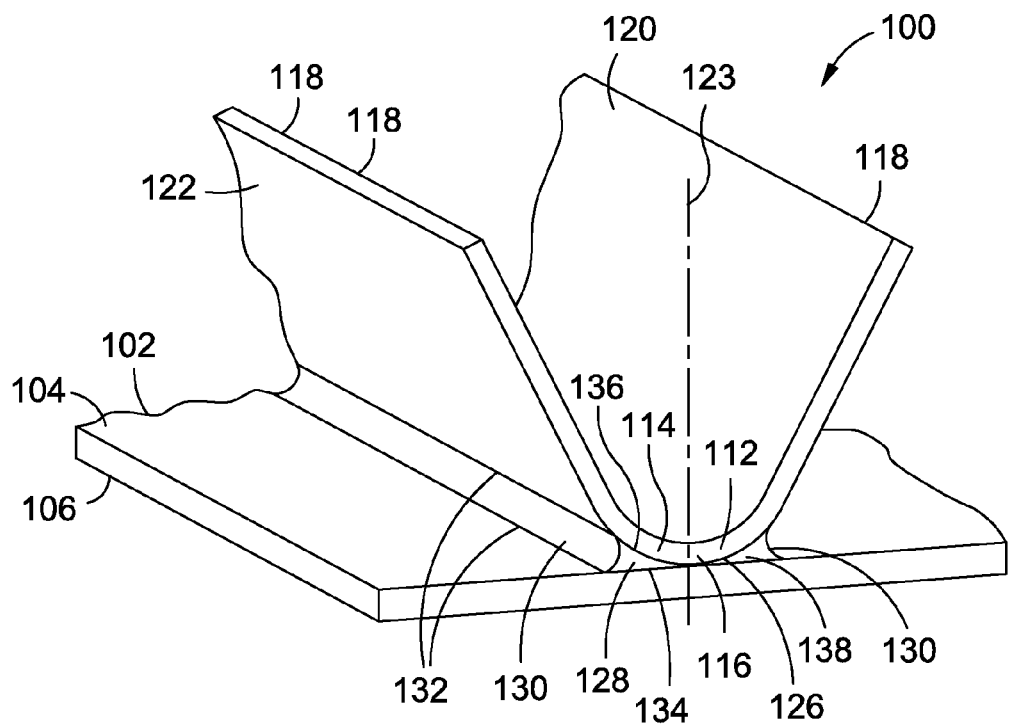
FIG. 2 is a perspective view of a fillet bond bonding one of the stiffeners to the skin panel.

Referring to FIG. 2, shown is a perspective view of a portion of a fillet bond 128 adhesively bonding one of the panel stiffeners 108 to the skin panel 102 of the structural assembly 100. The panel stiffener 108 is shown having a pair of legs 118 extending outwardly from a base portion 112 and forming a V-shape configuration. The base portion 112 is shown having a generally curved cross-sectional shape 114. Each one of legs 118 of the panel stiffener 108 may have an inner surface 120 and an outer surface 122. The apex 116 of the outer surface 106 of the base portion 112may be disposed in substantially contacting relation to the inner surface 104 of the skin panel 102 at the fillet bond 128. The fillet bonds 128 may include a fillet face 130 on each one of the opposing sides of the fillet bond 128. Each one of the fillet faces 130 may have a fillet edge 132 at an adhesive-skin interface 134 and a fillet edge 132 at an adhesive-stiffener interface 136.

Figure 3:
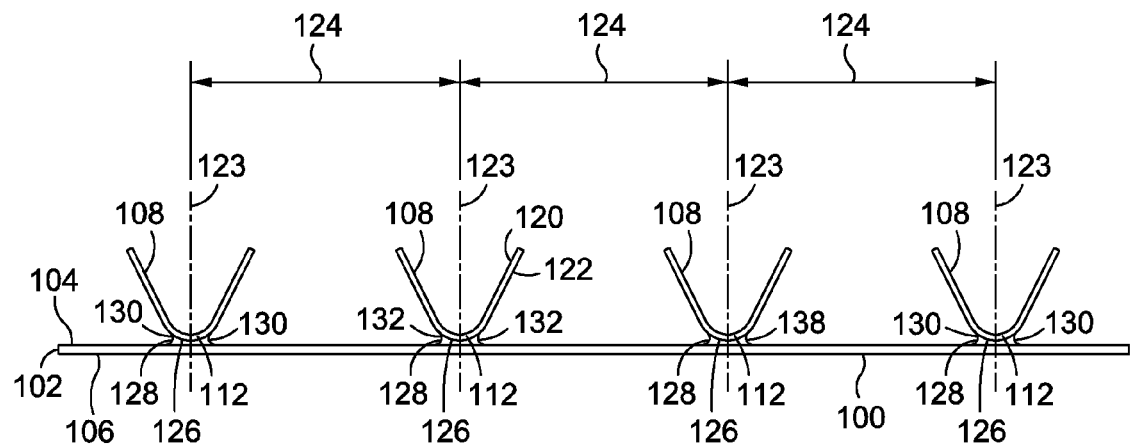
FIG. 3 is a side view of the structural assembly of FIG. 1 illustrating the stiffeners spaced apart from one another at a Stiffener pitch.

Referring to FIG. 3, shown is a side view of the structural assembly 100 of FIG. 1 illustrating the plurality of panel stiffeners 108 adhesively bonded to the inner surface 104 of the skin panel 102. The panel stiffeners 108 may be positioned in spaced relation to one another. For example, the panel stiffeners 108 may be spaced apart from one another at a uniform distance between the stiffener axes 123 defining a stiffener pitch 124. However, the panel stiffeners 108 may be provided at non-uniform spacings or at a combination of uniform and non-uniform spacings. In the embodiment shown, the panel stiffeners 108 may be formed of a fiber-reinforced material such as carbon fiber reinforced polymeric material. The skin panel 102 may be formed of a metallic material. However, the panel stiffeners 108 and the skin panel 102 may be formed of carbon fiber reinforced polymeric material, ceramic material, metallic material, or any combination thereof.

Figure 4:
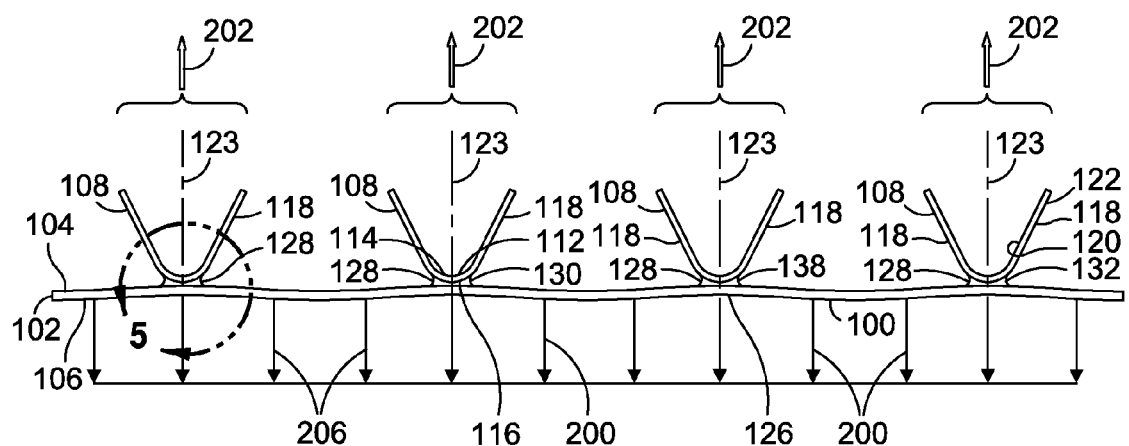
FIG. 4 is a side view of the structural assembly in a loaded condition wherein a tension pulloff load is applied to the skin panel.

Referring to FIG. 4, shown is a side view of the structural assembly 100 with a plurality of panel stiffeners 108 bonded to the skin panel 102 and spaced apart from one another at a stiffener pitch 124 (FIG. 3). A substantially uniformly-distributed tension pulloff load 200 is applied to the skin panel 102 which is reacted by a reaction force 202 at each one of the panel stiffeners 108. The testing apparatus 600 (FIG. 11) may be configured to duplicate, in the test specimen, the loading conditions that occur at the fillet bond 128 of a skin-stiffener joint 126 (FIG. 3) between the skin panel 102 and a panel stiffener 108 during application of a substantially uniformly distributed tension pulloff load 200. In this regard, the testing apparatus 600 advantageously provides a means for substantially duplicating the internal loads induced in the structural assembly 100 at the fillet bond 128 including the bending moment 204 (FIG. 5), the out-of-plane and/or in-plane shear force 206 (FIG. 5), and the tension load at a given location in the fillet bond 128 in response to a distributed load applied to the skin panel 102 stiffened with panel stiffeners 108.

Advantageously, the testing apparatus 600 (FIG. 11) provides a means for substantially duplicating the stresses occurring in the fillet bond 128 including peel loads at the fillet edges 132 (FIG. 2), shear stress and tension stress (e.g., mode I) at the adhesive-skin interface 134 (FIG. 2) due to bending loads in the skin component, stress within the adhesive, and other stresses. The test specimen 300 (FIG. 6) may be configured such that the fillet bond 328 (FIG. 6) is substantially similar to the fillet bond 128 in the structural assembly 100 represented by the test specimen 300. In this regard, the adhesive material 138 (FIG. 2) in the fillet bond 328 of the test specimen 300 may have bulk mechanical properties (e.g., strength, modulus of elasticity) that are similar to the bulk mechanical properties of the adhesive material 138 in the fillet bond 128 of the structural assembly 100. In addition, the skin component 302 (FIG. 6) and the stiffener component 308 (FIG. 6) of the test specimen 300 may have the same type and quality of surface treatment at the area of the fillet bond 328 as in the fillet bonds 128 of the structural assembly 100.

Figure 5:
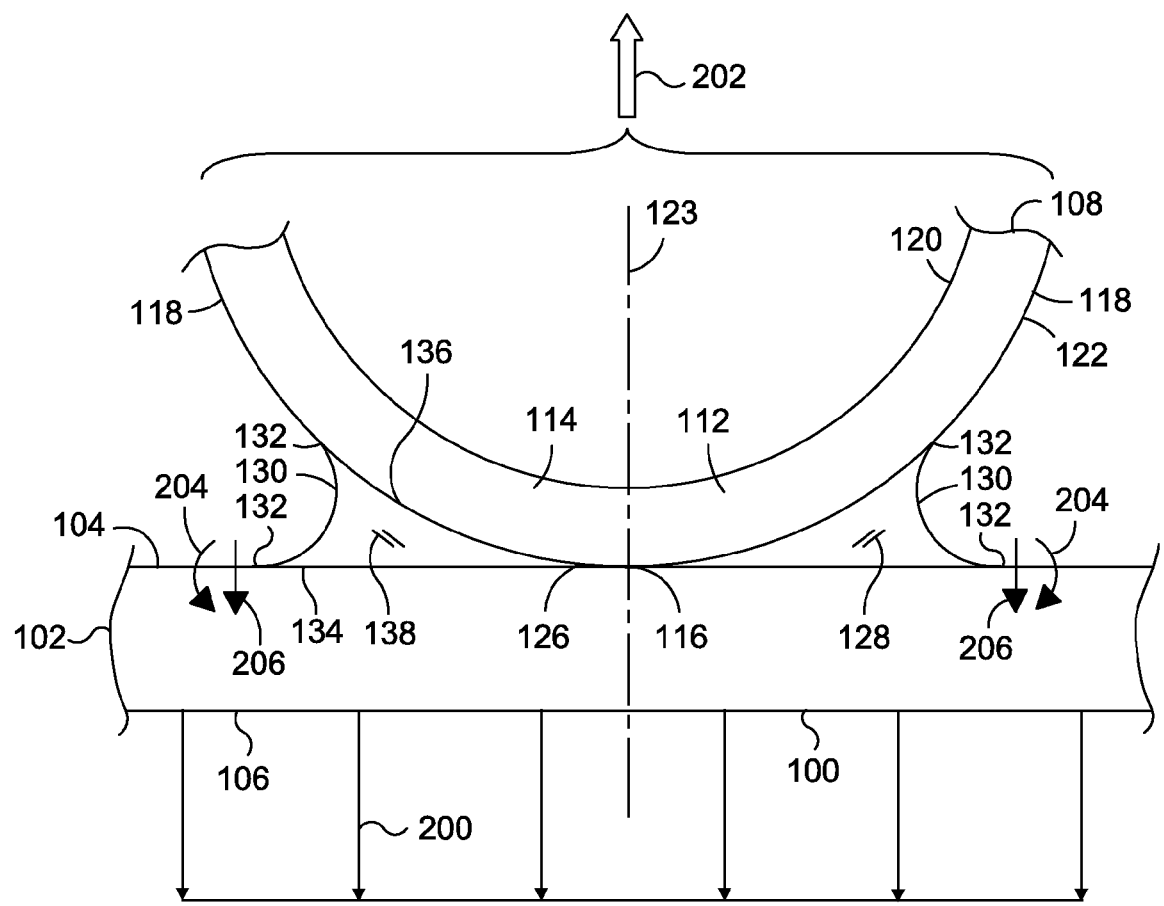
FIG. 5 is a side view of the fillet bond between one of the stiffeners and the skin panel.

Referring to FIG. 5, shown is a side view of the fillet bond 128 between the skin panel 102 and the base portion 112 of one of the panel stiffeners 108. The fillet bond 128 includes fillet faces 130 on opposing sides of the fillet bond 128. Although the fillet faces 130 are shown with a generally concave shape or configuration, the fillet faces 130 may be provided in any configuration including a planar configuration, a convex configuration, or any other shape or configuration. The apex 116 of the base portion 112 may be disposed in substantially contacting relation to the skin panel 102. Alternatively, the apex 116 may be positioned in slightly spaced relation with the skin panel 102 and a film of adhesive may extend between the apex 116 and the skin panel 102. The fillet bond 128 may include a fillet face 130 and a fillet edge 132 on each side of the fillet bond 128 at an adhesive-skin interface 134.

FIG. 5 further illustrates internal loads induced in the structural assembly 100 during application of a distributed tension pulloff load 200 applied to the skin panel 102 and reacted by a reaction force 202 at the panel stiffener 108. The internal loads may include a bending moment 204 and an out-of-plane shear force 206 on each side of the fillet bond 128 at each one of the fillet edges 132. Due to their distance form the stiffener axis 123, the fillet edges 132 on each side of the fillet bond 128 may comprise locations where induced loads within the fillet bond 128 or at the adhesive-skin interface 134 are relatively high.

Advantageously, the testing apparatus 600 (FIG. 11) disclosed herein provides a means for substantially duplicating the magnitude of the bending moment 204 (FIG. 5) and the magnitude of the shear force 206 (FIG. 5) induced in the fillet bond 128 (FIG. 5) in response to the application of a distributed tension pulloff load 200 (FIG. 5) to a skin panel 102. In this regard, the testing apparatus 600 provides a means for substantially duplicating a moment-shear ratio at a given location along the fillet bond 128 of a skin panel 102 stiffened with panel stiffeners 108. For example, the testing apparatus 600 provides a means for substantially duplicating the moment-shear ratio at the fillet edges 132 on opposite sides of the fillet bond 128 of a structural assembly 100 at the adhesive-skin interface 134 where induced loads may be relatively high and which may correspond to relatively high stresses within the adhesive material 138, at the adhesive-skin interface 134, and/or within the skin panel 102 material or panel stiffener 108 material.

Figure 6:
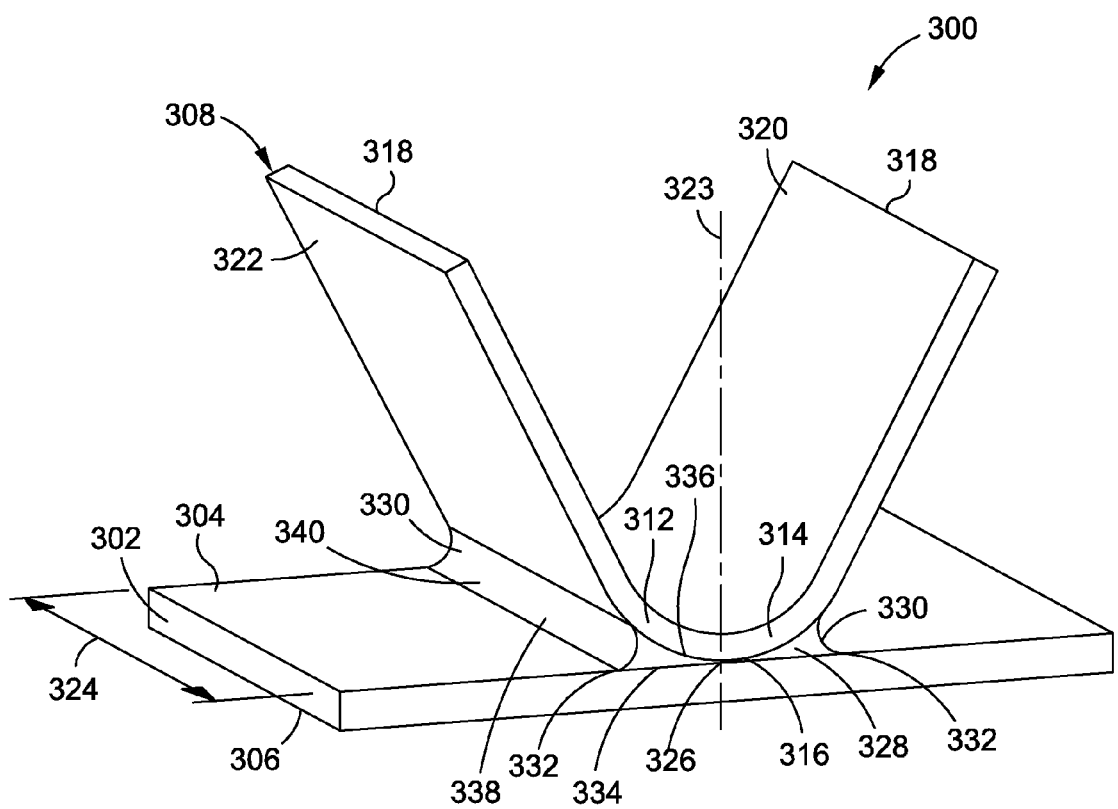
FIG. 6 is a perspective view of a test specimen having a stiffener component bonded to a skin component using a fillet bond wherein the test specimen may represent the fillet bond between a panel stiffener and the skin panel of the structural assembly.

Referring to FIG. 6, shown is a perspective view of a test specimen 300 which may be configured to represent a fillet bond 128 (FIG. 5) between a panel stiffener 108 (FIG. 5) and a skin panel 102 (FIG. 5) of a structural assembly 100 (FIG. 5). The test specimen 300 may include the stiffener component 308 and the skin component 302 joined at a skin-stiffener joint 326 with a fillet bond 328 extending along a fillet bond length 324 which may be substantially equivalent to the width of the test specimen 300. The skin component 302 may have inner and outer surfaces 304, 306. The stiffener component 308 may include inner and outer surfaces 320, 322 and a base portion 312 interconnecting a pair of legs 318 extending outwardly from the base portion 312. The legs 318 may be symmetrical about a stiffener axis 323. The fillet bond 328 may include a fillet face 330 on each one of the opposing sides of the fillet bond 328. Each one of the fillet faces 330 may have a fillet edge 332 at an adhesive-skin interface 334 and a fillet edge 332 at an adhesive-stiffener interface 336. The fillet faces 330 are shown having a concave 340 configuration.

The stiffener component 308 may have a geometry that may be substantially similar to the geometry of the panel stiffener 108 (FIG. 5) at least in the area of the fillet bond 128 (FIG. 5) of the structural assembly 100 (FIG. 5). Likewise, the skin component 302 may have a geometry that is substantially similar to the geometry of the skin panel 102 (FIG. 5) at least in the area of the fillet bond 128 of the structural assembly 100. For example, the skin component 302 may have a generally planar configuration to substantially duplicate the planar geometry of the skin panel 102 of the structural assembly 100. In an embodiment, the stiffener component 308 and the skin component 302 of the test specimen 300 may be formed of materials that are substantially similar to the materials from which the panel stiffener 108 and the skin panel 102 are formed to improve the accuracy of the tension test results.

Figure 7:
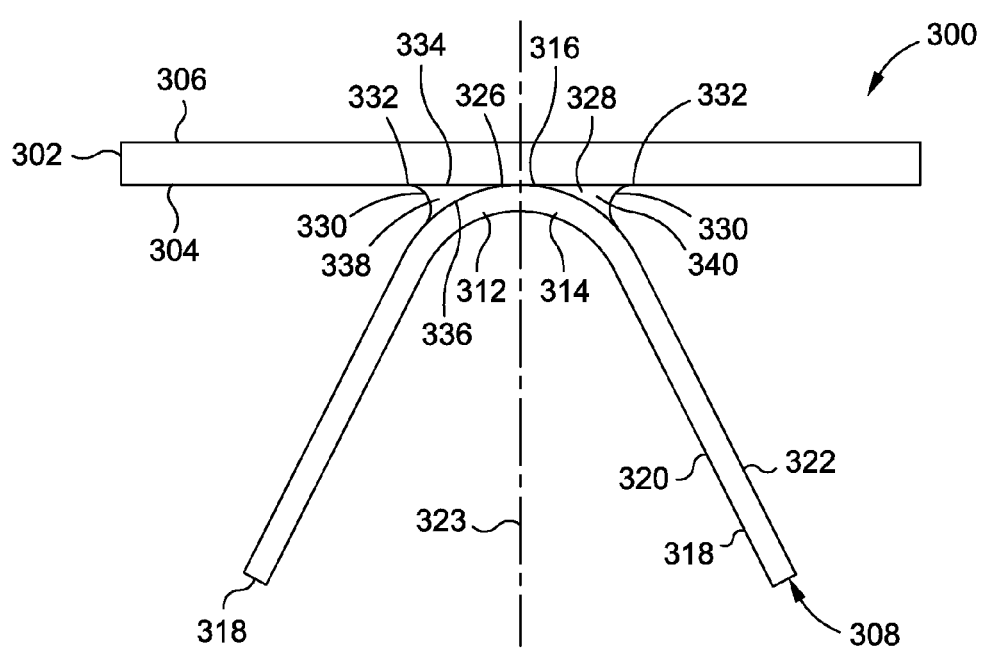
FIG. 7 is a side view of the test specimen of FIG. 6 wherein the test specimen is inverted and illustrating opposing sides of the fillet bond having fillet faces each having a concave configuration.

FIG. 7 is a side view of the test specimen 300 oriented such that the legs 318 of the stiffener component 308 extend generally downwardly from the fillet bond 328 in a V-shaped configuration. The test specimen 300 may be generally symmetrical about a stiffener axis 323 although the test specimen 300 may be asymmetric. In the embodiment shown, the stiffener axis 323 may bisect an angle formed between the legs 318 of the stiffener component 308. However, the legs 318 of the stiffener component 308 may be formed in any configuration that substantially duplicates the geometry of the legs 118 (FIG. 5) of a panel stiffener 108 (FIG. 5), at least in the area a fillet bond 128 (FIG. 5) of a structural assembly 100 (FIG. 5). Likewise, the skin component 302 may be formed in any configuration that substantially duplicates the geometry of the skin panel 102 (FIG. 5) of a structural assembly 100, at least in the area of a fillet bond 128 of the structural assembly 100.

Figure 8:
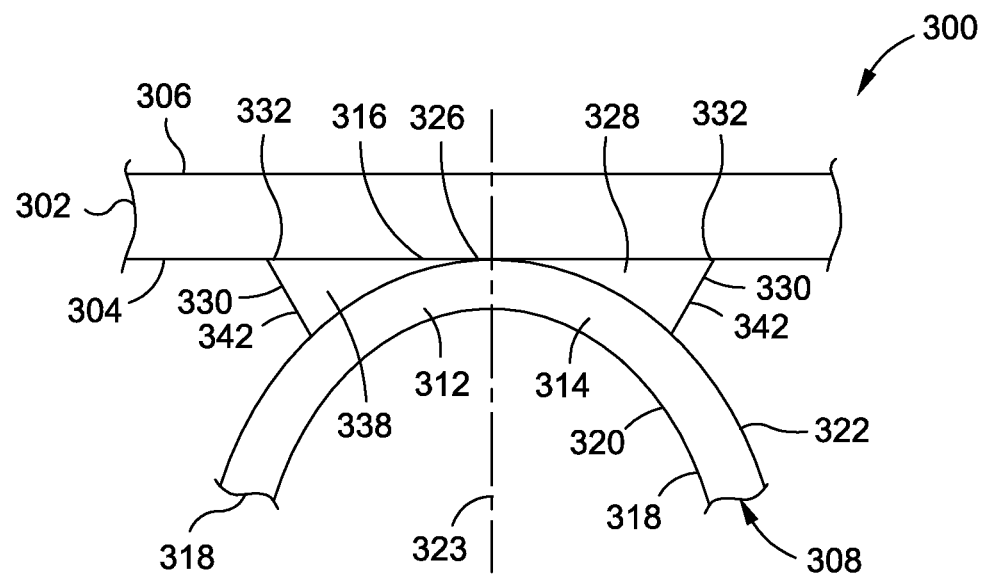
FIG. 8 is a side view of a fillet bond having fillet faces having a flat or planar configuration and oriented at a non-perpendicular angle relative to the skin component.
Figure 9:
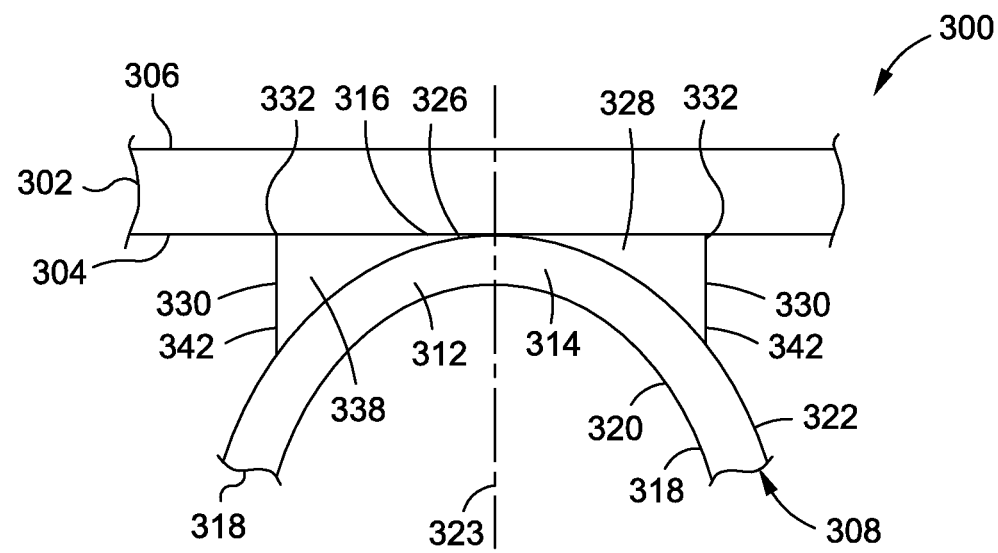
FIG. 9 is a side view of a fillet bond having fillet faces having a planar configuration and oriented at a perpendicular angle relative to the skin component.

FIG. 8 shows a test specimen 300 with a fillet bond 328 having fillet faces 330 with a generally planar 342 configuration oriented at a non-perpendicular angle relative to the inner surface 304 of the skin component 302. FIG. 9 shows a test specimen 300 with a fillet bond 328 having fillet faces 330 with a planar 342 configuration and oriented at a generally perpendicular angle relative to the skin component 302. As may be appreciated, the fillet bond 328 in a test specimen 300 may be configured such that the fillet faces 330 are provided with any one of a variety of different configurations that may substantially duplicate the fillet bond 128 (FIG. 5) between a panel stiffener 108 (FIG. 5) and a skin panel 102 (FIG. 5) of a structural assembly 100 (FIG. 5). In test specimen 300 disclosed herein, the thickness of the fillet bond 328 may vary from one side of the fillet bond 328 to an opposite side of the fillet bond 328 as shown in FIG. 8. Advantageously, the testing apparatus 600 (FIG. 10) provides a means for accurately characterizing the tension strength of variable thickness fillet bonds 328.

Figure 10:
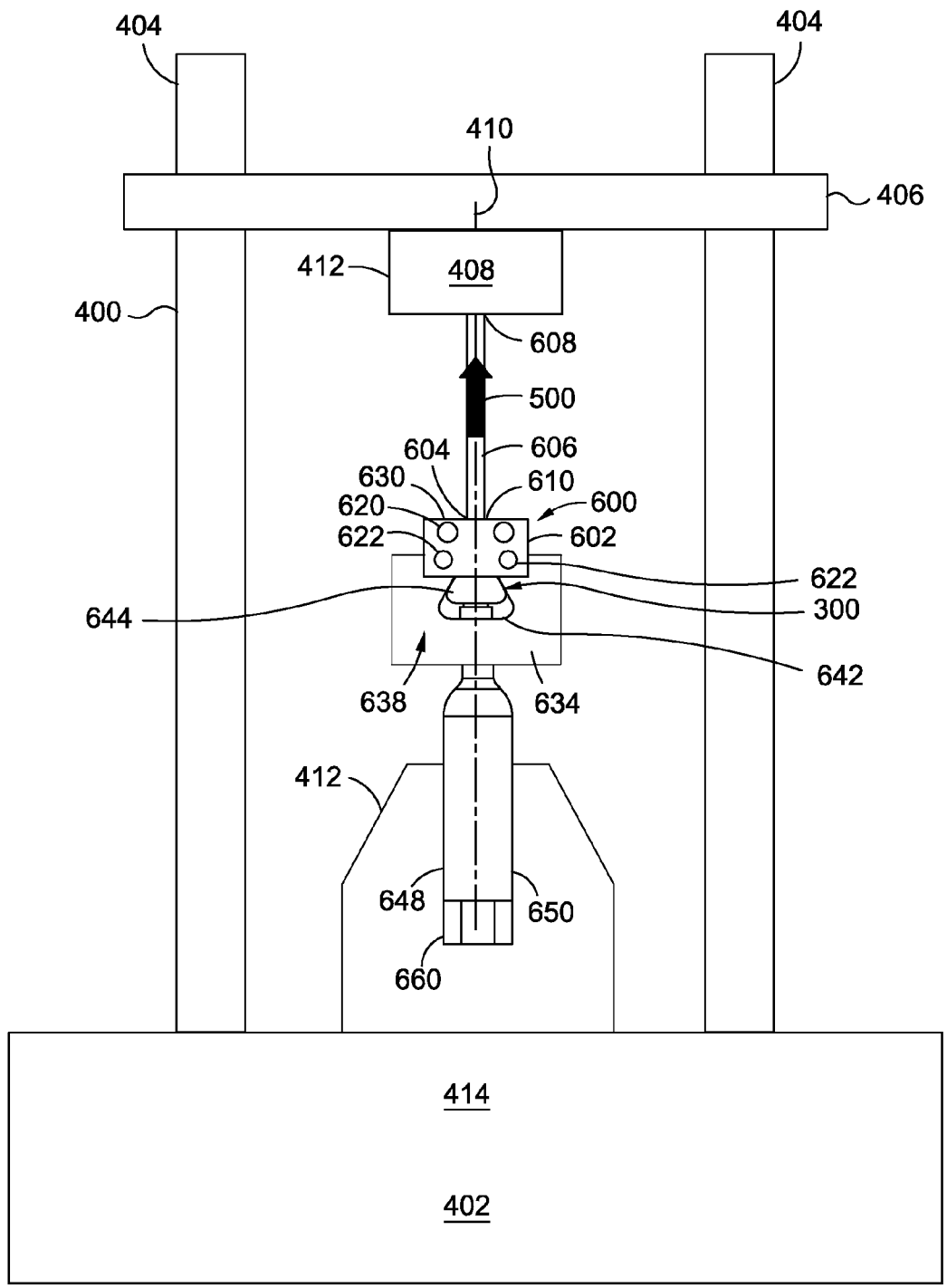
FIG. 10 is a side view of a universal testing machine having an embodiment of a testing apparatus mounted to the universal testing machine.

FIG. 10 is a side view of a universal testing machine 400 having a testing apparatus 600 mounted therewithin. In the embodiment shown, a test specimen 300 (FIG. 6) may be mounted within the testing apparatus 600 for testing the static tension strength of a fillet bond 328 (FIG. 6) of the test specimen 300. The testing apparatus 600 may support the test specimen 300 during application of a tension test load 500 to the test specimen 300 to characterize the tension load-carrying capability of the fillet bond 328. However, the testing apparatus 600 is not limited to static tension testing and may be implemented for performing durability and/or fatigue testing of the fillet bond 328.

In FIG. 10, the universal testing machine 400 may include a relatively rigid base 402 which may be mounted on a surface such as a bench or a floor of a test laboratory. The universal testing machine 400 may include a plurality of posts or columns 404 that may extend upwardly from the base 402. A crosshead 406 may extend across the columns 404. The crosshead 406 may be vertically movable for applying a tension test load 500 on the test specimen 300. The universal testing machine 400 may include an engagement mechanism such as a hydraulic grip 412 for gripping the gimbal rod 606 and a hydraulic grip 412 for gripping the shaft 648 of the testing apparatus 600. The hydraulic grips 412 may be quickly engaged and disengaged from the shaft 648 and the gimbal rod 606 to allow for relatively quick change-out of test specimens 300.

The universal testing machine 400 may include an actuator 414 for moving the crosshead 406 up and down for applying a tension test load 500 to the test specimen 300 mounted within the testing apparatus 600. The actuator 414 may be hydraulically powered, electrically powered, mechanically powered or a combination thereof or the actuator 414 may be powered by other suitable means. The universal testing machine 400 may include an axial load measuring device 408 such as a load cell. In the embodiment shown, the load measuring device 408 may be coupled to an upper rod end 608 of a gimbal rod 606 extending upwardly from a gimbal joint 604 included with the upper fixture 602 of the testing apparatus 600 as described below. The load cell may be configured to measure a magnitude of the tension test load 500 that may be applied to the test specimen 300 along a loading axis 410.

Figure 11:
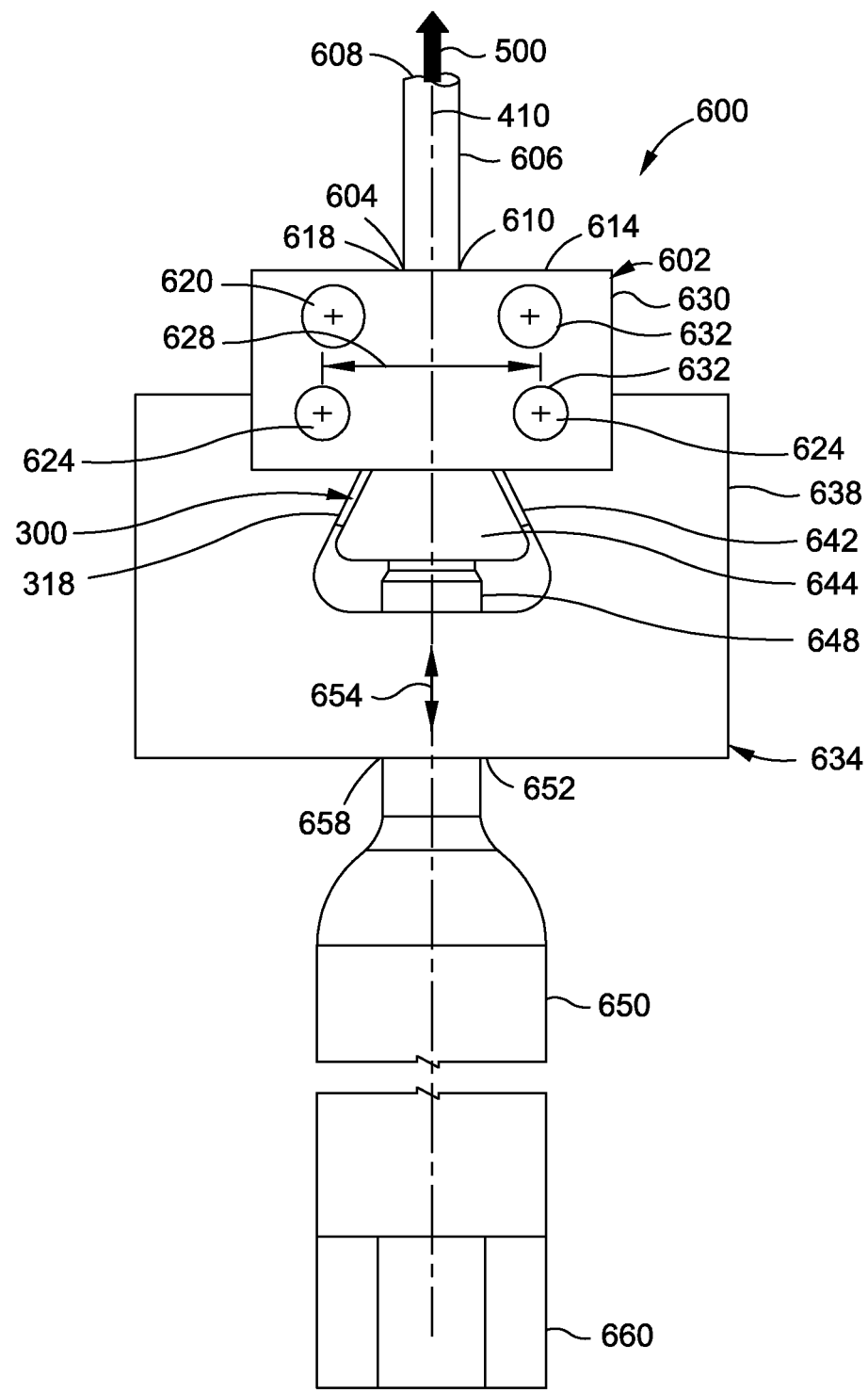
FIG. 11 is a side view of the testing apparatus having a fillet bond test specimen mounted therewithin.

FIG. 11 is a side view of the testing apparatus 600. The testing apparatus 600 may include a lower fixture 634 and an upper fixture 602. The lower fixture 634 may be configured to fixedly position or clamp the stiffener component 308 (FIG. 6) in position to prevent vertical and/or lateral movement thereof. The lower fixture 634 may include an outer clamping block and an inner clamping block 644. The outer clamping block may include a shaped cutout 642 for receiving the inner clamping block 644. The shaped cutout 642 of the outer clamping block and the inner clamping block 644 may be configured complementary to the geometry of the legs 318 of the test specimen 300.

The upper fixture 602 may be configured to engage the skin component 302 (not shown) at a pair of discrete engagement locations 626 (FIG. 13) on opposite sides of the fillet bond 328 (FIG. 6) of the test specimen 300 (FIG. 6). For example, the upper fixture 602 may include a pair of engagement devices 622 such as load pins 624 that may be positionable at the engagement locations 626 for applying a tension force 504 (FIG. 14) to the skin component 302 (FIG. 6) during application of a tension test load 500 through the gimbal rod 606. The engagement locations 626 may be spaced apart at an engagement location spacing 628 that may be selected to provide a desired moment-shear ratio at a given location in the fillet bond 328 such as at the fillet edges 332 of the adhesive-skin interface 334.

Figure 12:
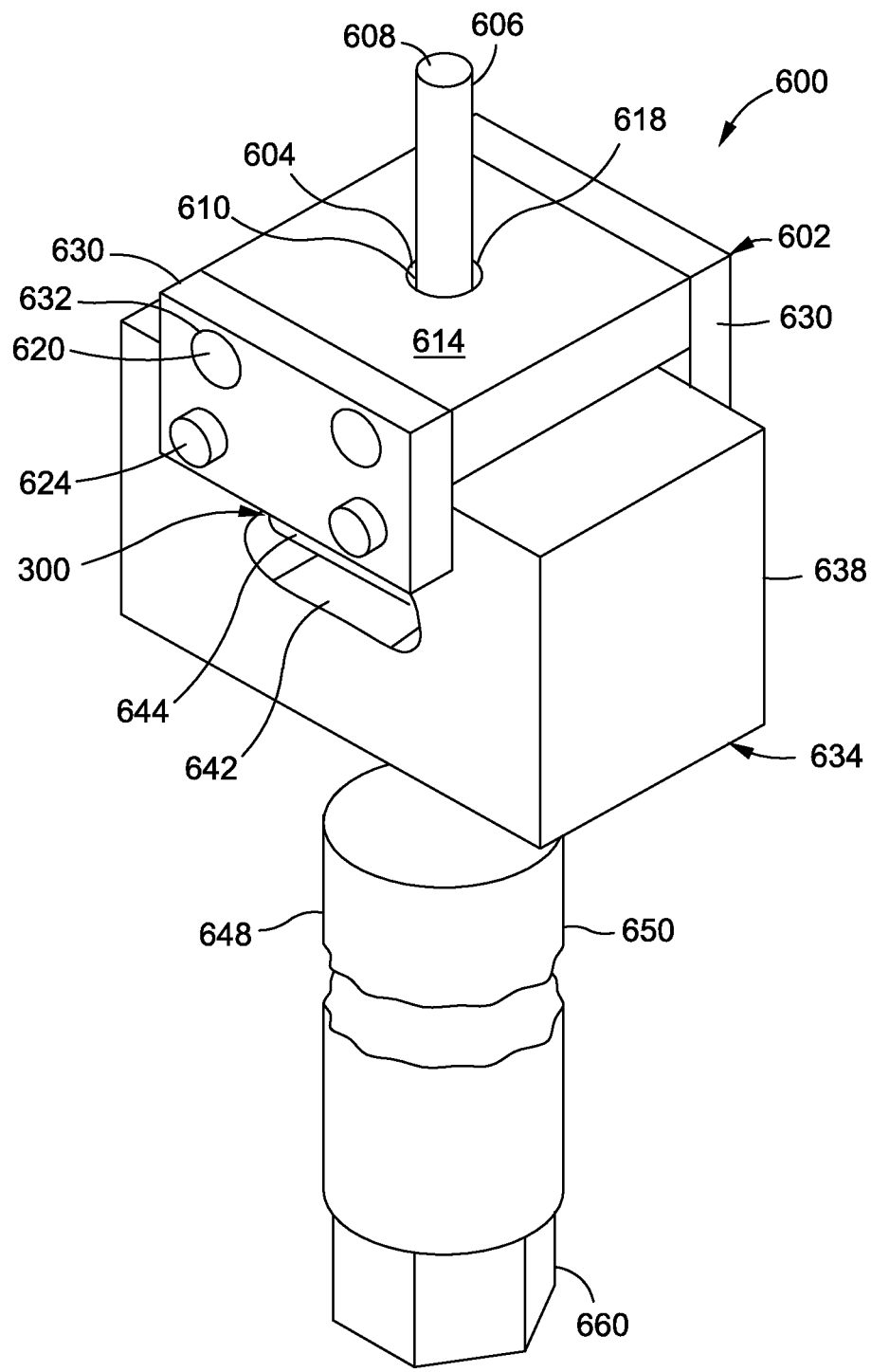
FIG. 12 is a perspective view of a testing apparatus.

FIG. 12 is a perspective view of the testing apparatus 600 illustrating a pair of side plates 630 that may be mounted on opposite sides of a gimbal plate 614 of the upper fixture 602. The side plates 630 may couple the engagement devices 622 (e.g., the load pins 624) to the gimbal joint 604. Each one of the side plates 630 includes pin bores 632 for receiving the load pins 624. The engagement devices 622 such as the load pins 624 may extend underneath the skin component 302

Figure 13:
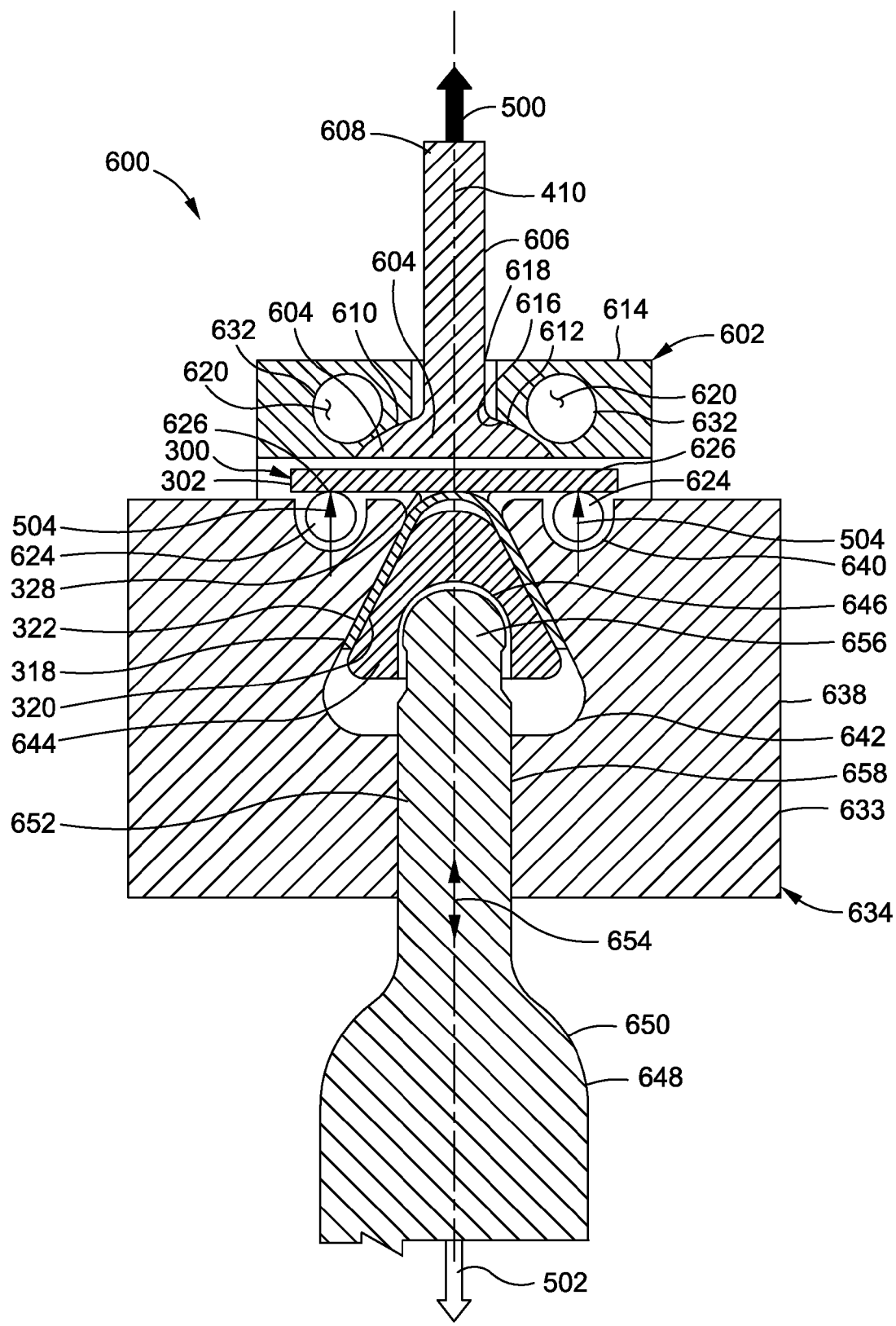
FIG. 13 is a section view of the testing apparatus including an upper fixture and a lower fixture for fixedly positioning the test specimen therewithin.

(FIG. 13). The plate pins 620 may couple the side plates 630 to the gimbal plate 614. When the actuator 414 (FIG. 10) of the universal testing machine 400 (FIG. 10) applies a tension test load 500 (FIG. 10), the load pins 624 may be placed into contact with the inner surface 304 (FIG. 6) of the skin component 302 (FIG. 6) at engagement locations 626 (FIG. 13).

In FIG. 13, the load pins 624 may be located at the engagement locations 626 which may be positioned at substantially equivalent distances from the fillet bond 328 on opposite sides thereof such that a substantially equivalent tension force 504 may be applied to the skin component 302 on each side of the fillet bond 328. The engagement location spacing 628 (FIG. 11) may be defined as the distance between the locations where tension force 504 is applied by the load pins 624. The load pins 624 may apply the tension force 504 to the skin component 302 as a point load or as a line load on each side of the fillet bond 328.

In an embodiment, the engagement location spacing 628 may be less than the stiffener pitch 124 (FIG. 3) of an adjacently-disposed pair of the panel stiffeners 108 (FIG. 3) of a structural assembly 100 (FIG. 3) represented by the test specimen 300. The engagement spacing 628 may be such that the skin component 302 may be loaded in bending and shear at a magnitude that is substantially equivalent to the bending and shear in the skin panel 102 (FIG. 3) at a fillet bond 128 (FIG. 3) of the structural assembly 100. The testing apparatus 600 may be configured such that the side plate having pin bores 632 that are spaced at one engagement location spacing 628 may be removed and replaced with a side plate having pin bores 632 spaced at a different engagement location spacing 628. By installing side plates 630 with a desired engagement location spacing 628 between the pin bores 632, a desired moment-shear ratio may be induced in the test specimen 300 at a given location (e.g., at the fillet edges 332) of the fillet bond 328 during tension testing.

FIG. 13 is a cross-sectional view of the testing apparatus 600 illustrating the interconnectivity of the upper and lower fixture 634 and the test specimen 300. The lower fixture 634 may be configured to clamp the stiffener component 308 (FIG. 6) in a fixed position as indicated above. The stiffener component 308 may include the base portion 312 (FIG. 6) and at least two legs 318 extending outwardly from the base portion 312. In the embodiment shown, the base portion 312 may have a generally curved cross-sectional shape 314 (FIG. 6). The base portion 312 may have an apex 316 (FIG. 6) which may be disposed in substantially contacting relation to the inner surface 304 (FIG. 6) of the skin component 306 (FIG. 6).

The legs 318 may form a V-shape with the base portion 312 (FIG. 6). The inner and outer clamping block 644, 638 may be configured complementary to the V-shape of the legs 318. However, the inner and outer clamping block 644, 638 may be configured complementary to any one of a variety of different stiffener component 308 (FIG. 6) configurations and are not limited to a shape that is complementary to V-shaped legs 318. Regardless of the shape or configuration of the stiffener component 308, the lower fixture 634 may be configured to fixedly clamp the legs 318 in a fixed position in such a manner that vertical and lateral movement of the legs 318 is prevented.

In an embodiment, the lower fixture 634 may include an adjustment mechanism 650 for adjusting the vertical position of the inner clamping block 644 relative to the shaped cutout 642 that may be formed in the outer clamping block. For example, the adjustment mechanism 650 may comprise a threaded portion 652 formed on a shaft 648 extending downwardly from the inner clamping block 644. The shaft 648 may have a rounded tip 656 shaped complementary to a rounded bore 646 that may be formed in the inner clamping block 644. The shaft 648 may extend downwardly from the inner clamping block 644 and may terminate at a hex end 660 (FIG. 12).

The threaded portion 652 may be threadably engaged to a threaded hole 658 formed in the outer clamping block 638. Rotation of a hex end 660 may facilitate adjustment of the position of the inner clamping block 644 along an axial adjustment direction 654 such that the inner and outer clamping block 644, 638 are movable into clamping engagement with respective ones of the inner and outer surfaces 320, 322 of the legs 318. In this manner, the test specimen 300 may be snugly clamped between the inner clamping block 644 and the outer clamping block 638. In addition, the threaded engagement of the shaft 648 with the outer clamping block 638 may facilitate relatively rapid installation and removal of different test specimens 300 when testing a large quantity of test specimens 300.

Figure 14:
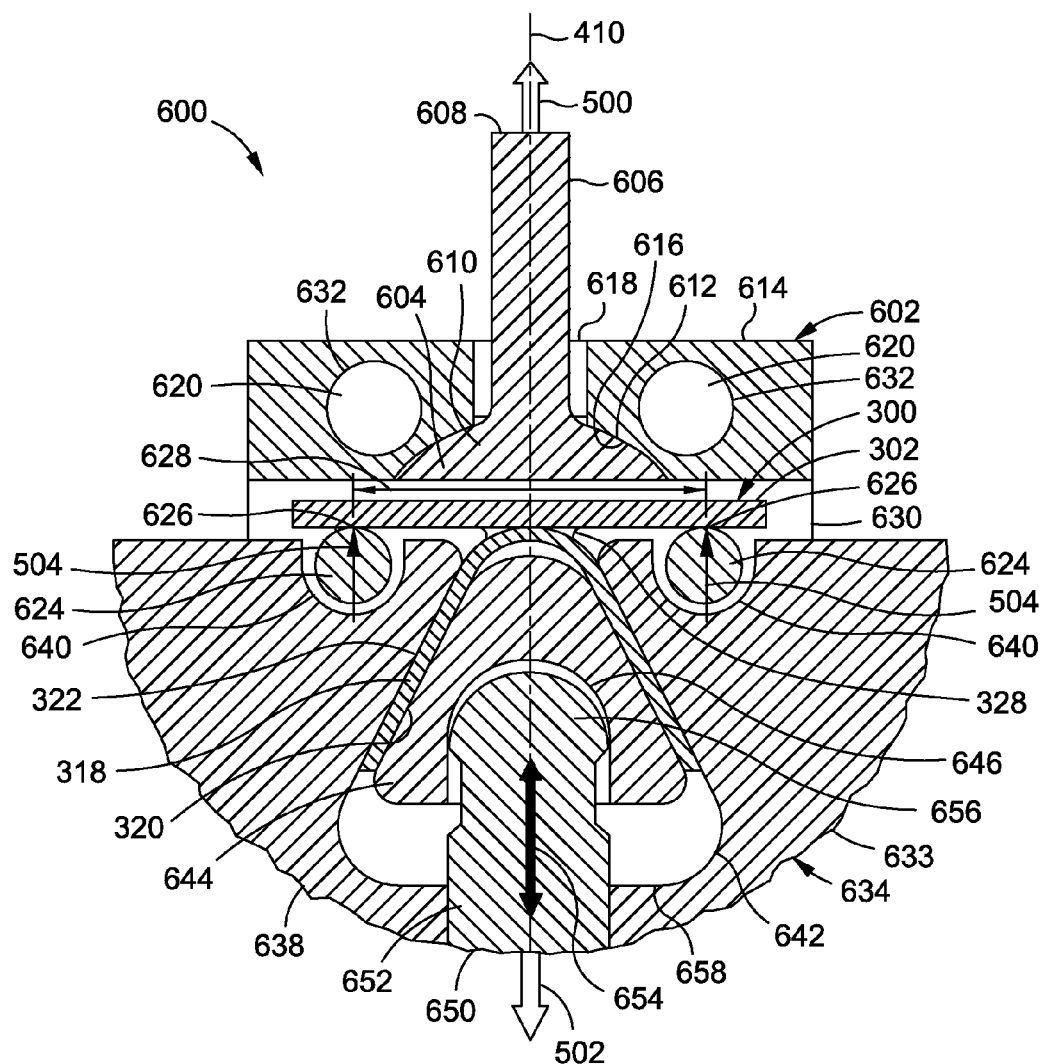
FIG. 14 is an enlarged view of the upper and lower fixture in illustrating a gimbal joint coupled to the upper fixture.

Referring to FIG. 14, the testing apparatus 600 may include a gimbal joint 604 that may be mechanically coupled to the upper fixture 602 via the gimbal plate 614. The gimbal plate 614 may include pin bores 632 that may be sized and configured for receiving a corresponding quantity of plate pins 620 coupling the gimbal plate 614 to the side plates 630. As indicated earlier, each one of the side plates 630 may include pin bores 632 for receiving engagement devices 622 such as the load pins 624 illustrated in FIG. 14. The load pins 624 and the plate pins 620 may be cylindrically shaped although the load pins 624 and plate pins 620 may be provided in a non-cylindrical embodiment. The outer clamping block 638 may include pin recesses 640 to provide clearance for the load pins 624. The load pins 624 may be oriented substantially parallel to a length of the fillet bond 328. The load pins 624 may be sized to provide resistance against bending of the load pins 624 during application of the tension force 504 to the inner surface 304 (FIG. 6) the skin component 302 (FIG. 6).

In FIG. 14, the gimbal joint 604 may be configured to substantially isolate the fillet bond 328 from asymmetric bending 510' (FIG. 25) and from asymmetric shear 512' (FIG. 25) as described in greater detail below. The gimbal joint 604 may include a gimbal rod 606. The gimbal rod 606 may extend upwardly through an aperture 618 formed in the gimbal plate 614. The gimbal rod 606 may have an upper rod end 608 and a lower rod end 610. The upper rod end 608 may be mechanically coupled to the load measuring device 408 (FIG. 10) such as the load cell illustrated in FIG. 10. The lower rod end 610 may have a spherical convex surface 612 that may be slidably engageable to a spherical concave surface 616 formed in the gimbal plate 614 such as on an underside of the gimbal plate 614. The gimbal plate 614 may be universally rotatable relative to the lower rod end 610. Application of the tension test load 500 through the upper fixture 500 may result in a reaction force 502 in the lower fixture 600.

It should be noted that the configuration of the gimbal joint 604 illustrated in FIG. 13 is not to be construed as limiting alternative configurations for the gimbal joint 604. In this regard, the gimbal joint 604 may be provided in any configuration that may facilitate reorientation 662 (FIG. 21) of the gimbal plate 614 and the engagement devices 622 in a manner allowing the engagement devices 622 (e.g., load pins 624) to apply a substantially equivalent tension force 504 to the engagement locations 626 on opposite sides of the fillet bond 328 of the test specimen 300. The gimbal joint 604 shown in FIG. 14 may be configured to provide a substantially universally angular range of motion relative to the tension loading axis 410 (FIG. 10).

In addition, the testing apparatus 600 may be configured such that the tension test load 500 is applied to the test specimen 300 through the gimbal joint 604 regardless of the angular orientation of the gimbal plate 614 and the engagement devices 622. Advantageously, the gimbal joint 604 may be configured such that the test specimen 300 is substantially isolated from the introduction of the above-mentioned asymmetric bending moments 510' (FIG. 25) and asymmetric shear forces 512' (FIG. 25) into the test specimen 300. The gimbal joint 604 may be configured to accommodate misalignment of the test specimen 300 with the universal testing machine 400 (FIG. 10). Such misalignment may be caused by manufacturing tolerances in the test specimen 300 or misalignments associated with the testing apparatus 600 and/or the universal testing machine 400. Advantageously, the gimbal joint 604 may improve the repeatability of applying a tension test load 500 to a plurality of test specimens 300. In this regard, the gimbal joint 604 may increase the accuracy of the test results.

Figure 15:
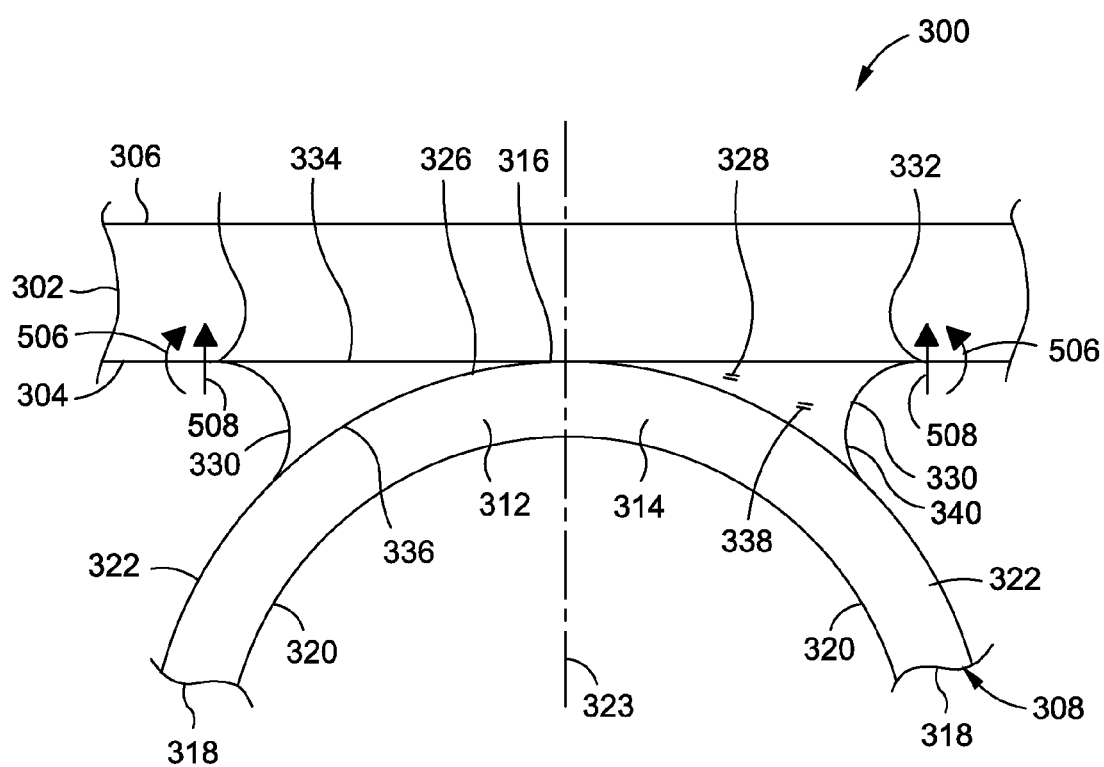
FIG. 15 is a side view of the fillet bond between the stiffener component and the skin component.

Referring to FIG. 15, shown is a side view of the fillet bond 328 between the stiffener component 308 and the skin component 302 and illustrating the bending moment 506 and out-of-plane shear force 508 that may be induced in the fillet bond 328 in response to the application of the tension force 504 (FIG. 14) on opposite sides of the fillet bond 328 as shown in FIG. 14. The tension force 504 applied by the load pins 624 (FIG. 14) to the skin component 302 at the engagement locations 626 (FIG. 14) on opposite sides of the bond line results in a pulling force being exerted on the fillet bond 328. As indicated above, each one of engagement locations 626 represents the location of the tension force 504 applied as a point load or a line load to the inner surface 320 of the skin component 302. Application of the tension force 504 allows the skin component 302 to bend in a manner similar to bending that may occur in the skin panel 102 (FIG. 5) of the structural assembly 100 as shown in FIG. 5. The tension force 504 applied to the skin component 302 may also result in an out-of-plane shear force 508 induced in the skin component 302 and/or fillet bond 328.

As indicated above, the engagement locations 626 (FIG. 14) may be spaced apart at an engagement location spacing 628 (FIG. 14) such that the bending moment 506 and the shear force 508 have a magnitude that is substantially similar to a magnitude of the bending moment 204 and shear force 206 induced in the fillet bond 128 of a structural assembly 100 subjected to a distributed tension pulloff load 200 as shown in FIG. 4. In this manner, the testing apparatus 600 provides a means for substantially duplicating a desired moment-shear ratio at the fillet edges 132 (FIG. 4) of the adhesive-skin interface 134 (FIG. 4) of the structural assembly 100. By providing a desired moment-shear ratio at the fillet edges 132, the strength characteristics of the fillet bond 328 (FIG. 14) may be accurately determined.

Figure 16:
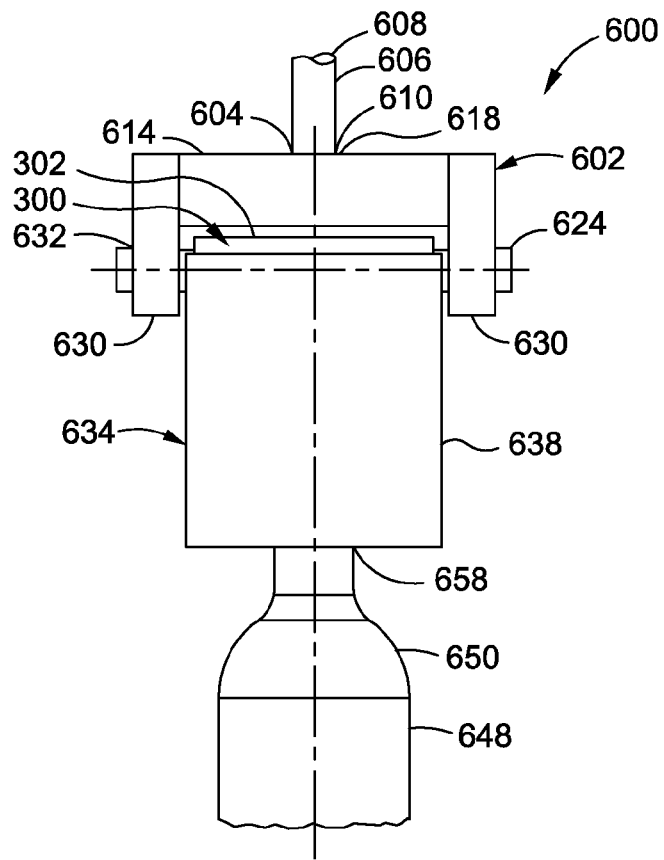
FIG. 16 is a side view of the testing apparatus and illustrating side plates mounted on opposite sides of the upper fixture.

Referring to FIG. 16, shown is a side view of the testing apparatus 600 illustrating the side plates 630 mounted on opposite sides of the gimbal plate 614. The side plates 630 extend downwardly along the sides of the outer clamping block. The load pins 624 are extended through pin bores 632 formed in the side plates 630. Although the load pins 624 are shown as being coupled to the gimbal joint 604 by means of the side plates 630 and the gimbal plate 614, the load pins 624 may be mechanically coupled to a gimbal joint 604 in any one of a variety of different configurations. For example, the side plates 630 and the gimbal plate 614 may be formed as a unitized structure. In this regard, the load pins 624 may be mechanically coupled to the gimbal joint 604 in any manner that facilitates substantially universal orientation of the load pins 624 relative to the gimbal rod 606.

Figure 17:
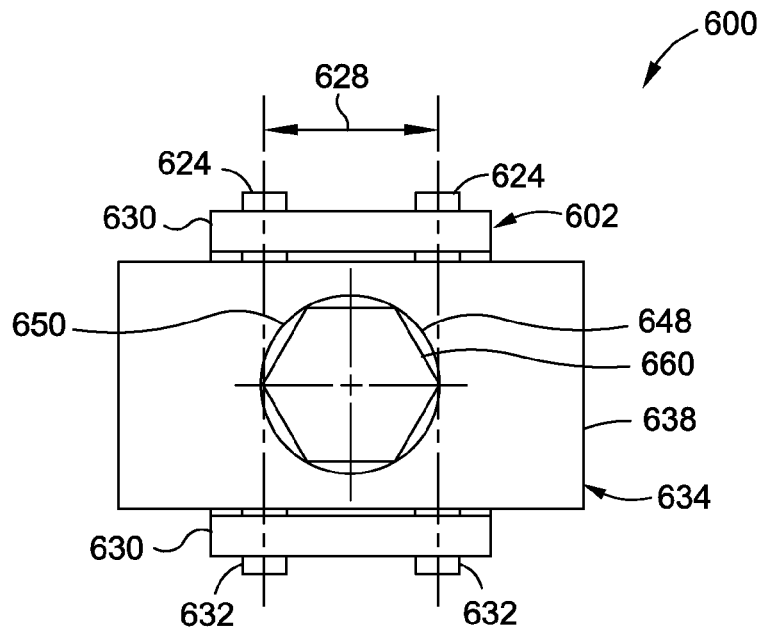
FIG. 17 is a bottom end view of the testing apparatus.

Referring briefly to FIG. 17, shown is a bottom view looking upwardly at the lower fixture 634. As indicated earlier, the shaft 648 (FIG. 14) may have a rounded tip 656 (FIG. 14) shaped complementary to a rounded bore 646 (FIG. 14) that may be formed in the inner clamping block 644 (FIG. 14). The shaft 648 may extend downwardly from the inner clamping block 644 (FIG. 14) and may terminate at a hex end 660. The hex end 660 may facilitate engagement of the shaft with a tool such as an open end wrench. In this manner, the hex end 660 may facilitate rotation of the shaft. Rotation of the shaft 648 may facilitate axial movement of the shaft 648 relative to the outer clamping block 638. Axial movement of the shaft 648 relative to the outer clamping block 638 may move the inner clamping block 644 axially relative to the shaped cutout 642 in the outer clamping block 638 shown in FIG. 13 in order to allow for installation and removal of a test specimen 300 from the testing apparatus 600. Advantageously, the threaded engagement of the shaft 648 with the outer clamping block 638 facilitates relatively rapid change-out of test specimens 300 when performing a series of tension tests.

Figure 18:
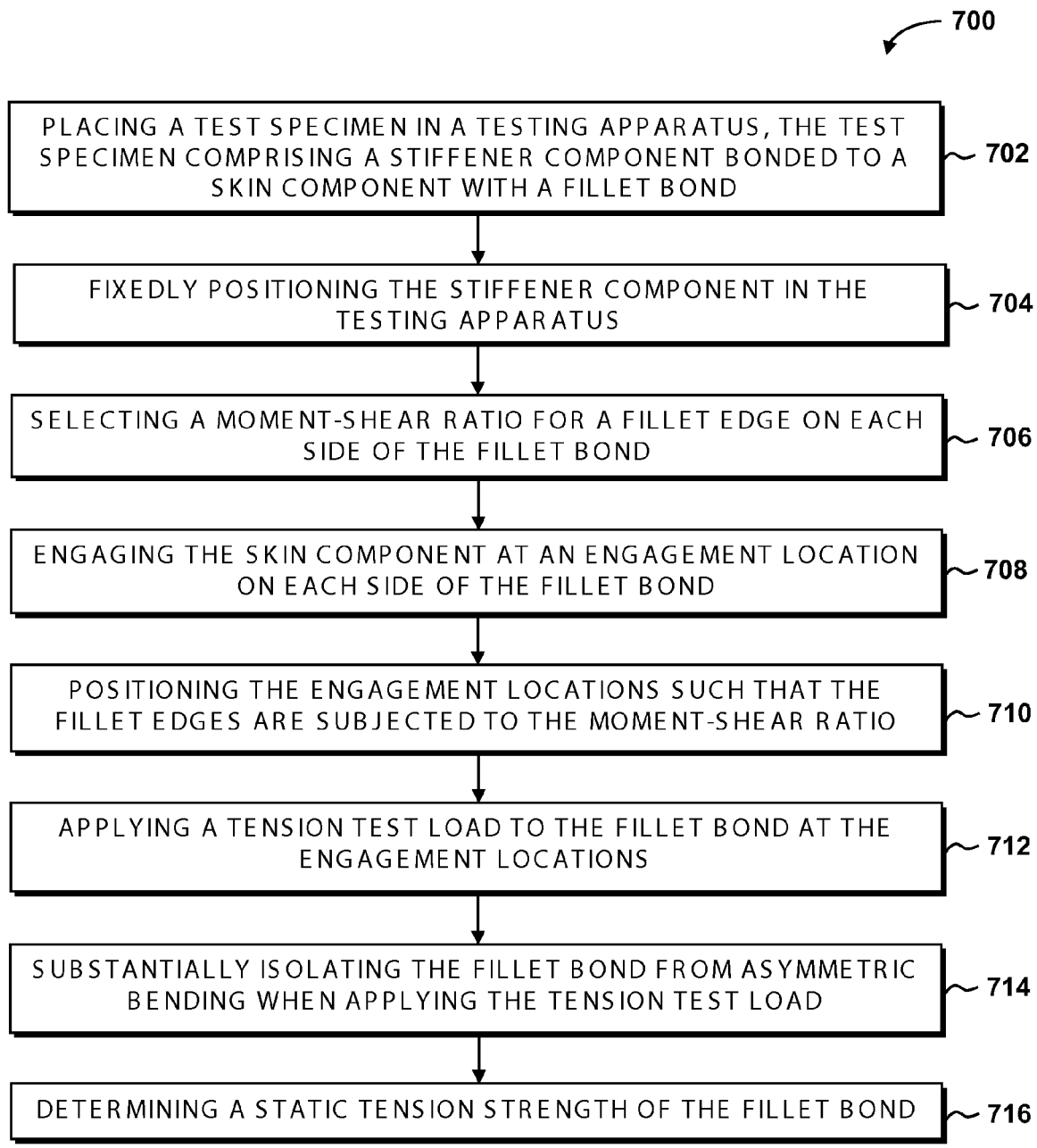
FIG. 18 is a flowchart illustrating one or more operations that may be included in a method for characterizing a tension strength of a fillet bond.
Figure 19:
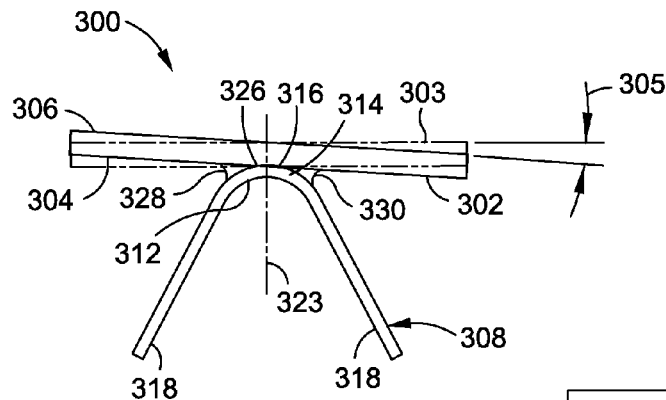
FIG. 19 is a side view of a test specimen having a skin component oriented at an angular offset relative to a nominal orientation of the skin component.

Referring to FIG. 18, shown is a flowchart having one or more operations that may be included in a method 700 of characterizing a tension strength of a fillet bond 328 (FIG. 13) joining a stiffener component 308 (FIG. 15) to a skin component 302 (FIG. 13) of a test specimen 300 (FIG. 15). Step 702 of the method may comprise installing a test specimen 300 in a testing apparatus 600. Advantageously, the testing apparatus 600 is configured to accommodate the testing of test specimens 300 where misalignment may exist in the test specimen 300 (FIG. 13), in the testing apparatus 600 (FIG. 13), and/or in the universal testing machine 400 (FIG. 10). For example, FIG. 19 illustrates a test specimen 300 having a skin component 302 (shown in solid) that is oriented at an angular offset 305 (e.g., a non-perpendicular orientation) relative to a nominal orientation 303 of the skin component 302 (shown in phantom).

Step 704 of the method 700 of FIG. 18 may comprise fixedly positioning the stiffener component 308 (FIG. 15) of the test specimen 300 (FIG. 13) by mounting the legs 318 of the stiffener component 308 within the lower fixture 634. For example, FIG. 13 illustrates the length of the lower fixture 634 clamped between the inner clamping block 644 and the shaped cutout 642 in the outer clamping block 638. Installation of a test specimen 300 in the testing apparatus 600 may comprise rotating the shaft 648 such that the inner clamping block 644 is lowered relative to the shaped cutout 642. The test specimen 300 may be installed such that the legs 318 are sandwiched between the inner clamping block 644 and the outer clamping block 638. The adjustment mechanism 650 may be adjusted to clamp the legs 318 between the inner and outer clamping blocks 644, 638. In this manner, the inner clamping block 644 may engage the inner surfaces 304 (FIG. 6) of the legs 318 and the outer clamping block 638 may engage the outer surfaces 306 (FIG. 6) of the legs 318 and thereby prevent lateral and vertical movement of the legs 318.

Step 706 of the method 700 of FIG. 18 may comprise selecting a moment-shear ratio for a fillet edge 332 (FIG. 6) of the fillet bond 328 (FIG. 6). As mentioned above, the moment-shear ratio may be selected to substantially duplicate a moment-shear ratio occurring at a fillet edge 132 of a structural assembly 100 under a substantially uniformly-distributed tension pulloff load 200 acting on a skin panel 102 stiffened by panel stiffeners 108 as illustrated in FIG. 3. The moment-shear ratio may comprise a ratio of bending moment 506 (FIG. 15) to shear force 508 (FIG. 15) induced in the skin component 302 (FIG. 6) at the fillet edge on each side of the fillet bond 328.

Figure 20:
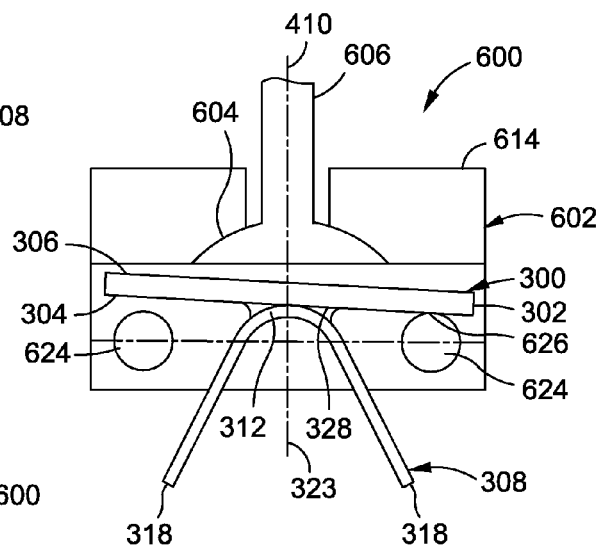
FIG. 20 is a side view of a test specimen mounted within a testing apparatus having a gimbal joint for isolating the test specimen from asymmetric bending and asymmetric shear.

Step 708 of the method 700 of FIG. 18 may comprise engaging the skin component 302 at the engagement locations 626 on opposite sides of the fillet bond 328. FIG. 20 illustrates the skin component 302 on the right hand side of the test specimen 300 being engaged by the load pin 624 and the skin component 302 on the left hand side of the test specimen 300 in spaced relation above the load pin 624.

Step 710 of the method 700 of FIG. 18 may comprise positioning the engagement location 626 (FIG. 20) on each side of the fillet bond 328 (FIG. 20) such that the tension test load 500 (FIG. 14) on each side of the fillet bond 328 results in the fillet edges 332 (FIG. 6) being subjected to the moment-shear ratio when the tension test load 500 is applied through the gimbal rod 606 (FIG. 20). As indicated above, the engagement location spacing 628 (FIG. 17) may be less than the stiffener pitch 124 (FIG. 3) between the panel stiffeners 108 (FIG. 3) of a structural assembly 100 (FIG. 3) having fillet bonds 128 (FIG. 3) of a configuration that is represented by the test specimen 300 (FIG. 6). The engagement location spacing 628 may be selected to produce a bending moment 506 (FIG. 15) and a shear force 508 (FIG. 15) of a magnitude that is substantially equivalent to the magnitude of the respective bending moment 204 (FIG. 5) and shear force 206 (FIG. 5) in the skin panel 102 (FIG. 3) of the structural assembly 100.

Figure 21:
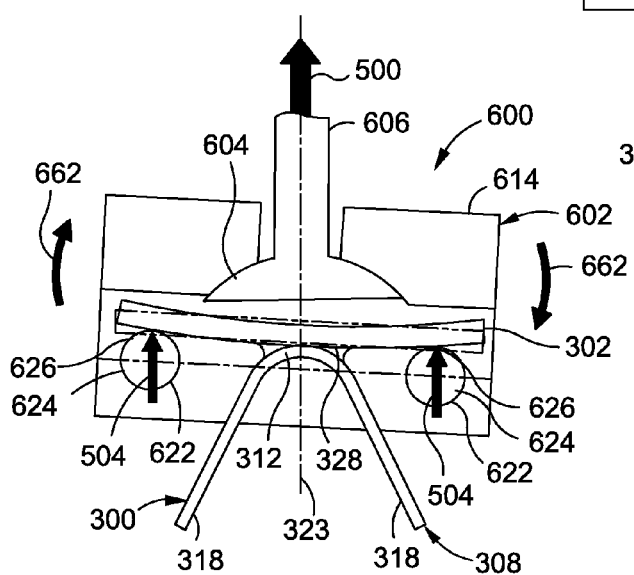
FIG. 21 is a side view of the test specimen subjected to a tension test load and illustrating the reorientation of the upper fixture such that the load pins applying a substantially equivalent tension force to each side of the fillet bond.

Step 712 of the method 700 of FIG. 18 may comprise applying a tension test load 500 to the fillet bond 328 at the engagement locations 626. FIG. 21 illustrates a tension test load 500 being applied along the gimbal rod 606. Advantageously, for test specimens 300 that may be misaligned with the upper fixture 602, the gimbal joint 604 causes an adjustment of the orientation of the upper fixture 602 which results in the adjustment in the orientation of the load pins 624 from the orientation shown in FIG. 20 to the orientation shown in FIG. 21. With the load pins 624 substantially aligned with the inner surface 304 (FIG. 20) of the skin component, a substantially equivalent tension force 504 may be applied to the skin component 302 on opposite sides of the fillet bond 328.

Figure 22:
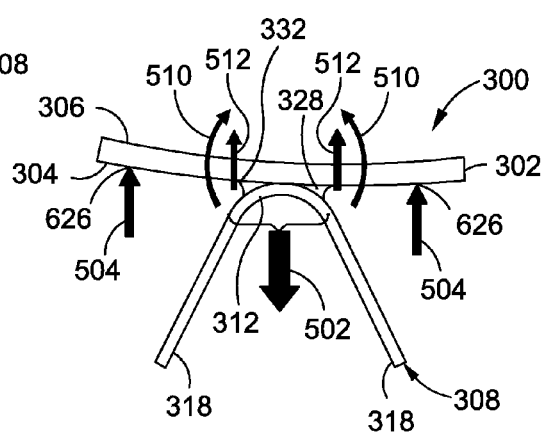
FIG. 22 is a loading diagram of the test specimen and illustrating symmetric bending and symmetric shear in the test specimen as a result of the reorientation of the upper fixture through the gimbal joint.

Step 714 of the method 700 of FIG. 18 may comprise substantially isolating the fillet bond 328 (FIG. 22) from asymmetric bending 510' (FIG. 25) when applying the tension test load 500 (FIG. 21). In this regard, the reorientation 662 (FIG. 21) of the load pins 624 (FIG. 21) facilitates the alignment of the load pins 624 with the inner surface 304 (FIG. 22) of the skin component 302 (FIG. 22) such that a substantially equivalent tension force 504 (FIG. 22) may be applied at the engagement locations 626 (FIG. 22) on each side of the fillet bond 328. The substantially equivalent application of tension force 504 at the engagement locations 626 may result in a substantially symmetric bending moment 510 and a substantially symmetric shear force 512 (FIG. 22) on each side of the fillet bond 328 at the fillet edge 332 as shown in the loading diagram of FIG. 22. In this regard, by including the gimbal joint 604 (FIG. 21) in the testing apparatus 600 (FIG. 21), asymmetric bending moment 510' (FIG. 25) and asymmetric shear force 512' (FIG. 25) on opposite sides of the fillet bond 328 may be avoided.

Figure 23:
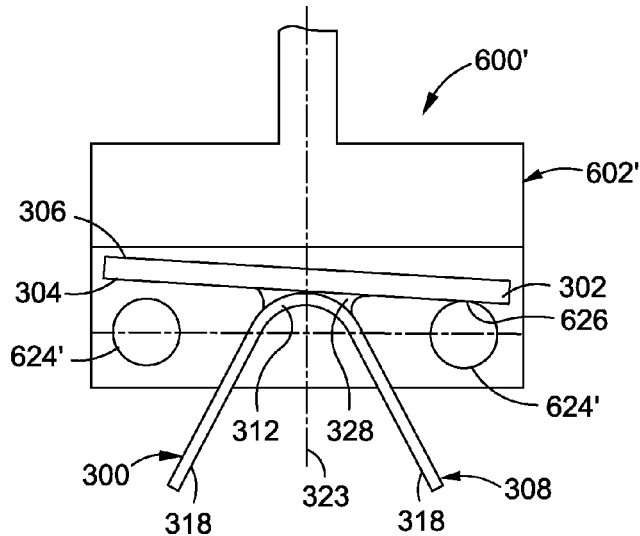
FIG. 23 is a side view of the test specimen of FIG. 19 mounted within a testing apparatus lacking a gimbal joint.
Figure 24:
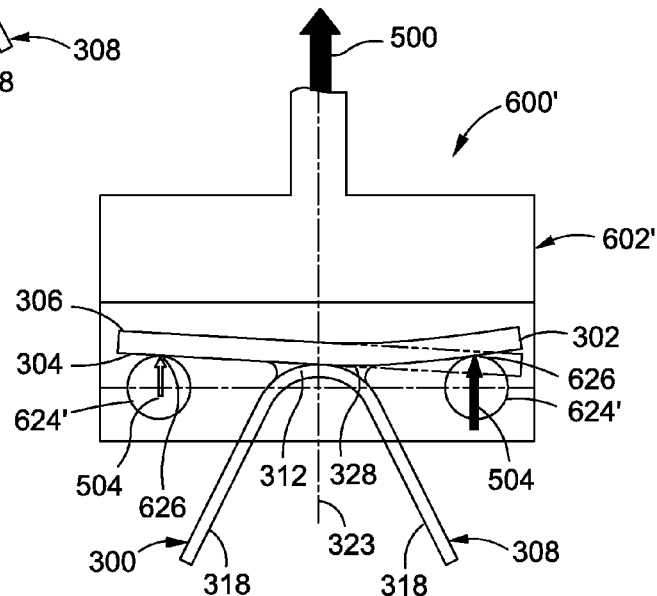
FIG. 24 is a side view of the test specimen subjected to a tension test load and illustrating increased bending on one side of the fillet bond relative to the bending on an opposite side of the fillet bond due to the angular offset of the skin component relative to a nominal orientation of the skin component.
Figure 25:
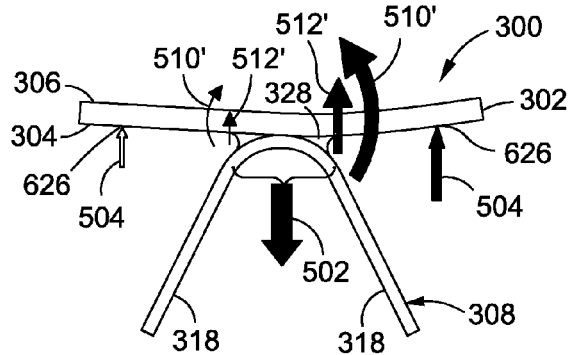
FIG. 25 is a loading diagram of the test specimen of FIG. 24 and illustrating asymmetric bending and asymmetric shear in the test specimen.

The avoidance of asymmetric bending 510' (FIG. 25) and asymmetric shear 512' (FIG. 25) may be illustrated by way of example with reference to FIGS. 23-25 which show a testing apparatus 600' for which the gimbal joint 604 (FIG. 21) is omitted. FIG. 23 illustrates the test specimen 300 mounted in the testing apparatus 600'. The load pin 624' on the right hand side of the fillet bond 328 is in contact with the skin opponent 302. However, the load pin 624' on the left hand side of the fillet bond 328 is disposed in spaced relation to the skin component 302. FIG. 24 illustrates the tension test load 500 being applied to the upper fixture 602'.

The loading diagram of FIG. 25 illustrates a tension force 504 applied to the skin component 302 on the right hand side and the left hand side of the fillet bond 328. Application of the tension test load 500 (FIG. 24) results in the load pin 624' (FIG. 24) on the right hand side of the fillet bond 328 (FIG. 24) contacting the inner surface 304 (FIG. 24) of the skin component 302 (FIG. 24) prior to the load pin 624' (FIG. 24) on the left hand side of the fillet bond 328 (FIG. 24) contacting the inner surface 304 (FIG. 24) of the skin component 302 (FIG. 24). Due to the angular offset 305 (FIG. 19) of the skin component 302 relative to the stiffener axis 323 (FIG. 24), the tension force 504 applied by the load pin 624' on the right hand side of the skin component 302 may be of greater magnitude than the tension force 504 applied by the load pin 624' on the left hand side of the skin component 302 resulting in asymmetric bending 510' and asymmetric shear 512' in the test specimen 300. The unequal tension forces 504 result in a bending moment and a shear force 508 on the right hand side of the skin component 302 that is of greater magnitude than the bending moment and the shear force 508 on the left hand side of the skin component 302. Such asymmetric bending moment 510' and asymmetric shear force 512' may compromise the accuracy of the test results.

Referring to FIG. 18, Step 716 of the method 700 may include determining a static tension capability or tension strength of the fillet bond 328 (FIG. 13). Advantageously, the testing apparatus 600 (FIG. 13) allows for directly determining the load-carrying capability of the fillet bond 328 and avoiding the need to measure and record strain or stress levels in the fillet bond 328 and then correlate the strain or stress levels to strength values as may be required in conventional structural testing. Advantageously, in the present disclosure, the static tension capability of a fillet bond 328 may be directly determined by recording the magnitude of the tension test load 500 (FIG. 13) at the failure of the fillet bond 328. The magnitude of the tension test load 500 at failure may be divided by the fillet bond length 324 (FIG. 6) to provide a bond strength of the fillet bond in terms of force unit per lineal unit such as pounds per inch.

The method may include generating test results in the form of strength values for a given fillet bond 328 (FIG. 6) configuration. The test results may include a description of the failure mode of the fillet bond 328. For example, the failure mode may comprise a cohesive failure of the adhesive material 338 (FIG. 6) within the fillet bond 328. The failure mode may also comprise an adhesive failure at an interface between the adhesive and the stiffener component 308 (FIG. 6) and/or at an interface between the adhesive and the skin component. The failure mode may further comprise a failure of one of the adherends (i.e., the skin component 302 and the stiffener component) such as a delamination and/or fracture of the skin component 302 (FIG. 6) material and/or the stiffener component 308 material, or other failure modes or combinations of failure modes. The test results may include a description of the environmental conditions (e.g., temperature of the test specimen, relative humidity) associated with each failure and the corresponding margin of safety of the fillet bond 328 as may be used for joint qualification and/or aircraft certification.

Additional modifications and improvements of the present disclosure may be apparent to those of ordinary skill in the art. Thus, the particular combination of parts described and illustrated herein is intended to represent only certain embodi-

What is claimed is:

1. A testing apparatus for characterizing a tension strength of a fillet bond joining a stiffener component to a skin component of a test specimen, the fillet bond having a fillet face on each one of opposing sides of the fillet bond, comprising:
a lower fixture configured to maintain the stiffener component in a fixed position;
an upper fixture having a pair of engagement devices positionable on opposite sides of the fillet bond and configured to engage the skin component at substantially equal distances from the fillet faces such that substantially equivalent tension forces are applied to the skin component on each side of the fillet bond during application of a tension test load on the test specimen; and
a gimbal joint mechanically coupled to the upper fixture and being configured to substantially isolate the fillet bond from asymmetric bending during application of the tension test load to the fillet bond.

2. The testing apparatus of claim 1, wherein:
the engagement devices are mechanically coupled to the gimbal joint.

3. The testing apparatus of claim 1, wherein:
the engagement devices comprise cylindrical load pins engageable to an inner surface of the skin component on opposite sides of the fillet bond; and
the load pins being oriented substantially parallel to a length of the fillet bond.

4. The testing apparatus of claim 1, wherein:
the stiffener component includes a base portion and at least two legs extending outwardly from the base portion; and
the lower fixture being configured to fixedly clamp the legs in the fixed position in a manner preventing vertical and lateral movement of the legs.

5. The testing apparatus of claim 1, wherein:
the lower fixture includes an outer clamping block and an inner clamping block configured to clamp a pair of legs therebetween.

6. The testing apparatus of claim 5, wherein:
the lower fixture includes an adjustment mechanism for adjusting a position of the inner clamping block relative to the outer clamping block such that the inner and outer clamping block are movable into clamping engagement with respective ones of inner and outer surfaces of the legs.

7. The testing apparatus of claim 1, wherein:
the fillet bond of the test specimen is configured substantially similar to a fillet bond of a structural assembly having a plurality of panel stiffeners adhesively bonded to a skin panel subjected to a substantially uniformly-distributed tension pulloff load acting on the skin panel, the fillet bond of the structural assembly having fillet edges on opposite sides of the fillet bond;
the fillet bond has a fillet edge on opposite sides of the fillet bond; and
each one of the engagement devices being substantially equidistantly positioned at a distance from the fillet bond such that the fillet edges are subjected to a moment-shear ratio that is substantially equivalent to the moment-shear ratio at the fillet edges of the structural assembly.

8. The testing apparatus of claim 7, wherein:
at least one adjacently-disposed pair of the panel stiffeners of the structural assembly are spaced apart from one another at a stiffener pitch; and
the engagement devices of the test specimen being spaced apart from one another at an engagement location spacing that is less than the stiffener pitch.

9. The testing apparatus of claim 1, wherein:
the skin component has a generally planar configuration.

10. A testing apparatus for characterizing a tension strength of a fillet bond joining a stiffener component and a skin component of a test specimen, the fillet bond having a fillet face on each one of opposing sides of the fillet bond, comprising:
a lower fixture configured to maintain the stiffener component in a fixed position;
an upper fixture having a pair of load pins being oriented generally parallel to one another and configured to engage an inner surface of a skin component at substantially equal distances from the fillet faces such that substantially equivalent tension forces are applied to the skin component on each side of the fillet bond during application of a tension test load on the test specimen;
a gimbal joint mechanically coupled to the upper fixture and being configured to substantially isolate the fillet bond from asymmetric bending during application of the tension test load to the fillet bond; and
the load pins being positioned such that fillet edges of the fillet bond are subjected to a moment-shear ratio that is substantially equivalent to the moment-shear ratio at the fillet edges of a structural assembly subjected to a uniformly distributed tension pulloff load.

11. A method of characterizing a tension strength of a fillet bond joining a stiffener component to a skin component of a test specimen, the fillet bond having a fillet face on each one of opposing sides of the fillet bond, comprising the steps of:
placing the test specimen in a testing apparatus;
fixedly positioning a stiffener component in a lower fixture of the test specimen;
engaging the skin component using a pair of engagement devices of an upper fixture of the testing apparatus, the engagement devices being positioned on opposite sides of the fillet bond at substantially equal distances from the fillet faces;
applying a tension test load to the fillet bond using the pair of engagement devices;
applying, using the engagement devices, substantially equivalent tension forces to the skin component on each side of the fillet bond during application of the tension test load; and
substantially isolating the fillet bond from asymmetric bending when applying the tension test load.

12. The method of claim 11, wherein the step of engaging the skin component using the pair of engagement devices comprises:
engaging an inner surface of the skin component using the pair of engagement devices.

13. The method of claim 11, wherein the step of engaging the skin component comprises:
engaging the skin component with two substantially parallel load pins in contact with an inner surface of the skin component on opposite sides of the fillet bond in an orientation substantially parallel to a length of the fillet bond; and
mechanically coupling the load pins to a gimbal joint.

14. The method of claim 11, further comprising the step of:
preventing lateral and vertical movement of a pair of legs of the stiffener component.

15. The method of claim 14, wherein the step of preventing lateral and vertical movement of each one of a pair of legs comprises:

clamping the legs between an outer clamping block and an inner clamping block.

16. The method of claim 15, further comprising the step of:
adjusting, using an adjustment mechanism, a position of the inner clamping block relative to the outer clamping block such that the inner and outer clamping blocks are movable into clamping engagement with inner and outer surfaces of the legs.

17. The method of claim 11, further comprising the step of:
determining a static tension test load-carrying capability of the fillet bond by dividing a bond length by a magnitude of the tension test load recorded at failure of the fillet bond.

18. The method of claim 11, wherein each one of the sides of the fillet bond includes a fillet edge at an adhesive-skin interface, the step of engaging the skin component comprises the steps of:
selecting a moment-shear ratio for the fillet edge comprising a ratio of a bending moment to a shear force at the fillet edge, the moment-shear ratio being substantially equivalent to a moment-shear ratio at a fillet edge of a structural assembly under a substantially uniformly-distributed tension pulloff load acting on a skin panel stiffened by panel stiffeners; and positioning the engagement devices on each side of the fillet bond such that the tension test load on each side of the fillet bond causing the fillet edge to be subjected to the moment-shear ratio when applying the tension test load.

19. The method of claim 18, wherein each side of the fillet bond includes a fillet edge at an adhesive-skin interface, the step of engaging the skin component comprises:
locating each one of the engagement devices at a distance from the fillet edge such that the fillet bond at each one of the fillet edges is subjected to the moment-shear ratio.

20. The method of claim 18, wherein the step of engaging the skin component at engagement locations comprises:
positioning the engagement devices at an engagement location spacing that is less than a stiffener pitch between at least one adjacently-disposed pair of panel stiffeners of a structural assembly under a substantially uniformly-distributed tension pulloff load acting on the skin panel.

* * * * *